(12) United States Patent
Barry et al.

(10) Patent No.: US 7,504,232 B2
(45) Date of Patent: Mar. 17, 2009

(54) METHOD OF SCREENING FOR INHIBITORS OF OSTEOPONTIN

(75) Inventors: Simon Barry, Macclesfield (GB); Carmel Horgan, Stevenage (GB); Steven Ludbrook, Stevenage (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 378 days.

(21) Appl. No.: 10/239,555

(22) PCT Filed: Mar. 23, 2001

(86) PCT No.: PCT/GB01/01287

§ 371 (c)(1),
(2), (4) Date: Mar. 17, 2003

(87) PCT Pub. No.: WO01/71358

PCT Pub. Date: Sep. 27, 2001

(65) Prior Publication Data

US 2003/0186325 A1 Oct. 2, 2003

(30) Foreign Application Priority Data

Mar. 23, 2000 (GB) .................. 0007101.9
Mar. 13, 2001 (GB) .................. 0106146.4

(51) Int. Cl.
*G01N 33/53* (2006.01)
*C07K 7/06* (2006.01)

(52) U.S. Cl. ........................ 435/7.8; 530/328

(58) Field of Classification Search .............. None
See application file for complete search history.

(56) References Cited

FOREIGN PATENT DOCUMENTS

| WO | WO 98/56405 | 12/1998 |
|---|---|---|
| WO | WO 99/08730 | 2/1999 |
| WO | WO 00/63236 | 10/2000 |

OTHER PUBLICATIONS

Curley et al. Integrin Antagonists; Cellular and Molecular Life Sciences, vol. 56 (1999) pp. 427-441.*
Bautista et al. Inhibition of Arg-Gly-Asp (RGD)-Mediated Cell Adhesion to Osteopontin by a Monoclonal Antibody Against Osteopontin; The Journal of Biological Chemistry, vol. 269, No. 37 (1994) pp. 23280-23285.*
Yokosaki et al. The Integrin Alpha-9-Beta-1 Binds to a Novel Recognition Sequence (SVVYGLR) in the Trombin-Cleaved Amino-Terminal Fragment of Osteopontin; The Journal of Biological Chemistry, vol. 274, No. 51 (1999) pp. 36328-36334.*
Colman, P.M. Effects of Amino Acid Sequence Changes on Antibody-Antigen Interactions; Researc in Immunology, vol. 145, No. 1 (1994) pp. 33-36.*
Lederman et al. A Single Amino Acid Substitution in a Common African Allele of the CD4 Molecule Ablates Binding of the Monoclonal Antibody, OKT4; Molecular Immunology, vol. 28, No. 11 (1991) pp. 1171-1181.*
Li et al. Beta-Endorphin Omission Analogs: Dissociation of Immunoreactivity From Other Biological Activities; Proc. Natl. Acad. Sci. vol. 77, No. 6 (1980) pp. 3211-3214.*
Abaza et al. Effects of Amino Acid Substitutions Outside an Antigenic Site on Protein Binding to Monoclonal Antibodies of Predetermined Specificity Obtained by Peptide Immunization: Demonstration With Region 94-100 (Antigenic Site 3) of Myoglobin; J. Prot. Chem. vol. 11, No. 5 (1992) pp. 433-444.*
Lim et al. Reach-Through Patent Claims in Biotechnology; An Analysis of the Examination Practices of the United States, European and Japanese Patent Offices; Intellectual Property Research Institute of Australia, Working Paper No. 03/05 (2005) pp. 1-62.*
Yokosaki et al. The Integrin Alpha 9 Beta 1 Binds to a Novel Recognition Sequence (SVVYGLR) in the Thrombin-Cleaved Amino-Terminal Fragment of Osteopontin; The Journal of Biological Chemistry, vol. 274, No. 51 (1999) pp. 36328-36334.*
Bayliss, et al., "Osteopontin is a ligand for the $\alpha_4\beta_1$ integrin", Journal of Cell Science, 111: 1165-1174 (1998).
Barry, et al., "A Regulated Interaction between α5β1 Integrin and Osteopontin", Biochemical and Biophysical Research Communications, 267: 764-769 (2000).
Bayless, et al., "Identification of dual $\alpha_{4)\beta(sub1}$ Integrin binding sites within a 38 amino acid domain in the N-terminal thrombin fragment of human osteopontin", Journal of Biological Chemistry, 10: 1074 (2001).
Barry, et al., "Analysis of the α4β1 Integrin_osteopontin Interaction", Experimental Cell Research, 258: 342-351 (2000).
Marcinkiewicz, et al., "Inhibitory Effects of MLDG-containing Heterodimeric Disintegrins Reveal Distinct Structural Reaquirements for Interaction of the Integrin α9β1 with VCAM-1, Tenascin-C, and Osteopontin", The Journal of Biological Chemistry, 275(41): 31930-31937 (2000).
Bayless, et al., "Identification of Dual $\alpha_4\beta_1$ Integrin Binding Sites within a 38 Amino Acid Domain in the N-terminal Thrombin Fragment of Human Osteopontin", The Journal of Biological Chemistry, 276(16): 13483-13489 (2001).
PCT International Search Report.
Fields, et al; Int. J. Peptide Protein Res.; 1990; 35; 161-214.
Kohler and Milstein; Nature; 1975; 256; 495-497.
Lin, et al; J. Med. Chem; 1999; 42; 920-934.
Merrifield, et al; Adv Enzymol; 1969; 32; 221-96.

* cited by examiner

*Primary Examiner*—Jon P Weber
*Assistant Examiner*—Paul C. Martin
(74) *Attorney, Agent, or Firm*—Jason C. Fedon; Edward R. Gimmi

(57) ABSTRACT

Amino acids (136 to 142) and amino acids (162 to 168) of human osteopontin constitute two sites at which osteopontin interacts with α4 integrins. Products capable of disrupting those interactions are useful in therapy, particularly in the treatment of inflammatory diseases.

14 Claims, 13 Drawing Sheets

Figure 1 --Prior Art--

A --Prior Art--
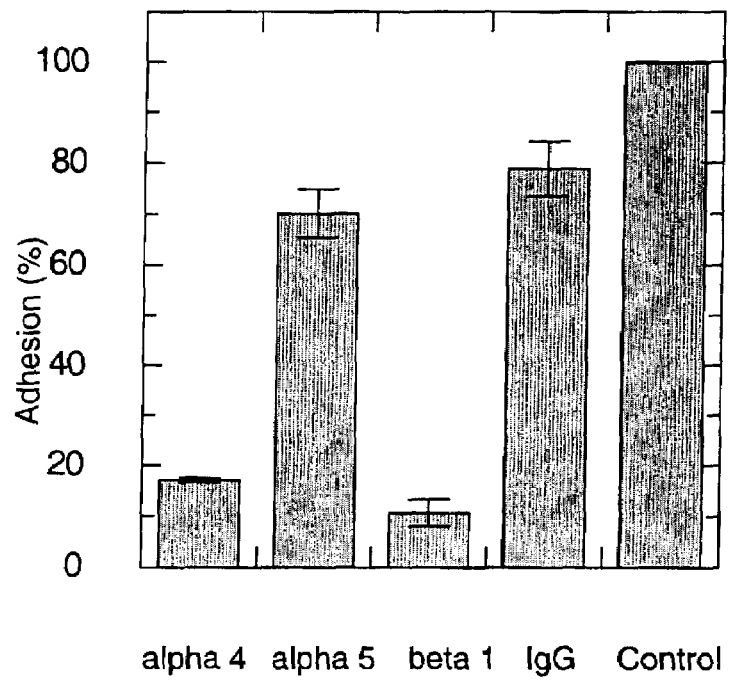
B
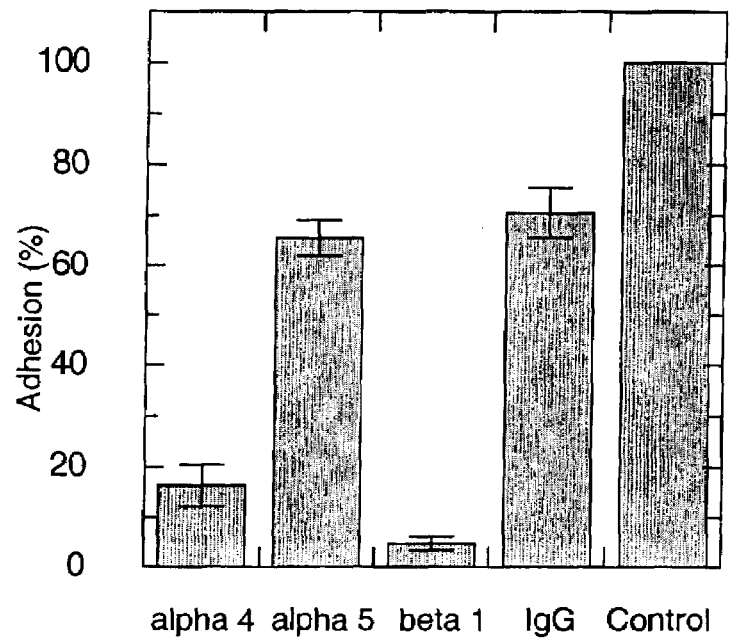
Figure 2

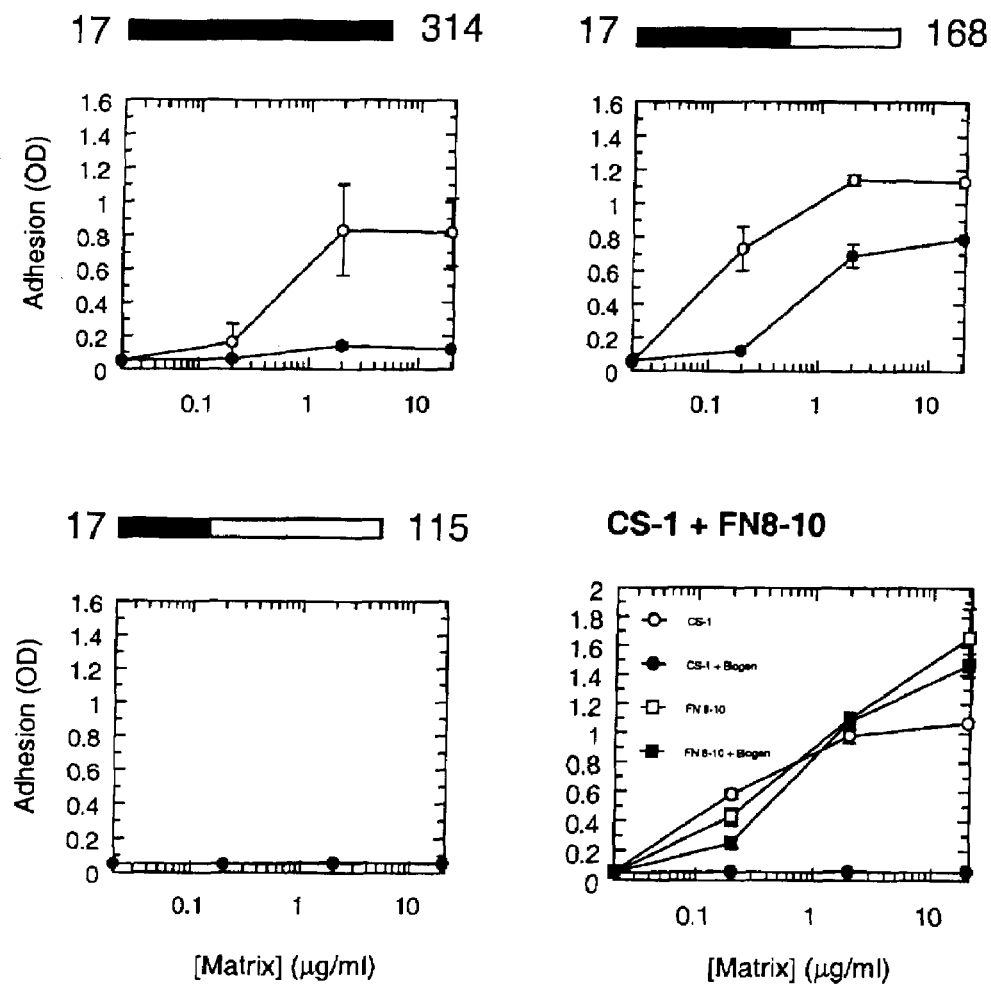
Figure 3 --Prior Art--

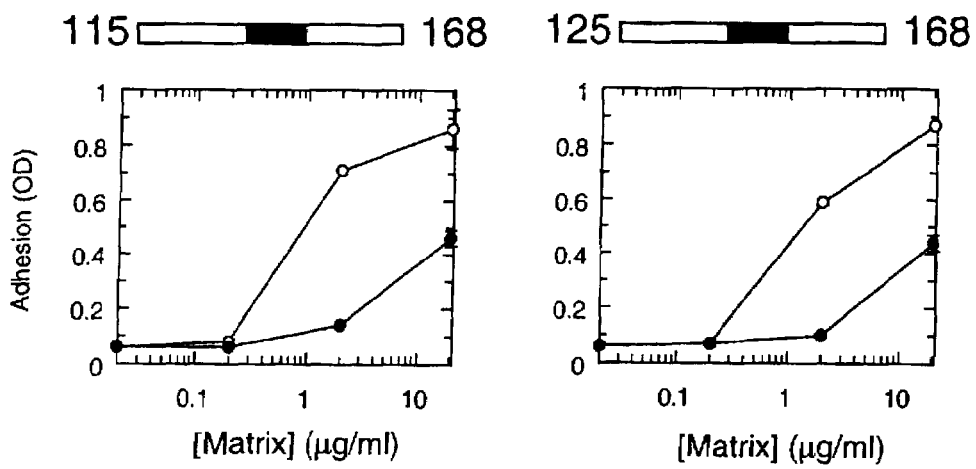
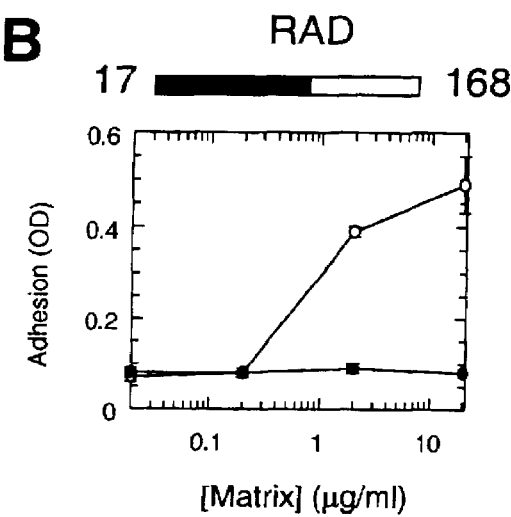
Figure 4 --Prior Art--

A
125 HSDESDELVTDFPTDLPATEVFTPVVPTVDTYDGRGDSVVYGLR 169 (SEQ ID NO:43)
125 HSDESDELVTDFPTD 139 (SEQ ID NO:44)
132 LVTDFPTDLPATEVF 146 (SEQ ID NO:45)
139 DLPATEVFTPVVPTV 153 (SEQ ID NO:46)
146 FTPVVPTVDTYDGRG 160 (SEQ ID NO:47)
153 VDTYDGRGDSVVYGLR 168 (SEQ ID NO:48)
B
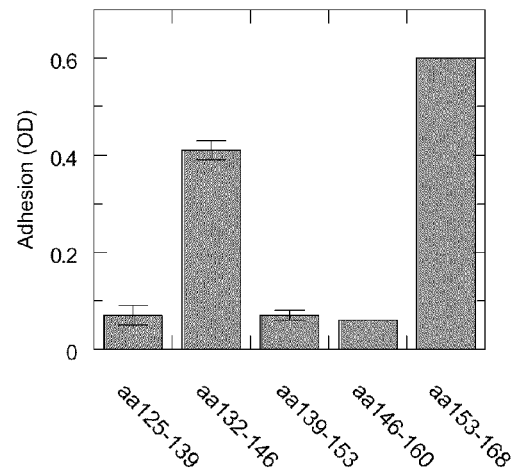
C
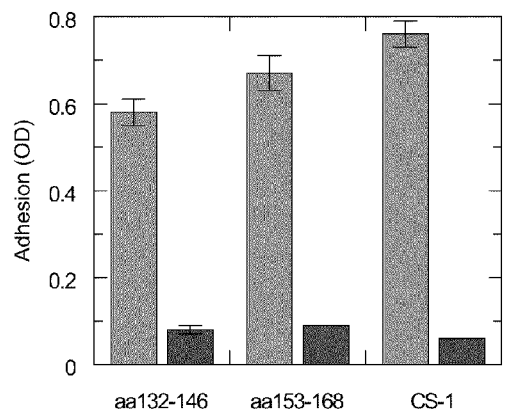
Figure 5

FIGURE 6

| | | |
|---|---|---|
| Human | ...HSDESDELVTDFPTDLPATEVFTPVVPTVDTYDGRGDS<u>VVYGLR</u> | (SEQ ID NO:43) |
| Bovine | ...HSDESD—EVDFPTDIPTIAVFTPFIPTESANDGRGDSVAYGLK | (SEQ ID NO:49) |
| Pig | ...HSDESDELVTDFPTDTP-ATDVTPAVPTGDPNDGRGDSVVYGLR | (SEQ ID NO:50) |
| Rabbit | HQSDESD-EVTVYPTEDAATTVFTEVVPTVETYDGRGDSVAYRLKR | (SEQ ID NO:51) |
| Rat | ...HSDESD—ESF-TASTQADVLTPIAPTVDVPDGRGDSLAYGLR | (SEQ ID NO:52) |
| Mouse | ...HSDESD—ETV-TASTQADTFTPIVPTVDVPNGRGDSLAYGLR | (SEQ ID NO:53) |

US 7,504,232 B2

METHOD OF SCREENING FOR INHIBITORS OF OSTEOPONTIN

FIELD OF THE INVENTION

The invention relates to medical products and, in particular, products for use in the treatment of diseases associated with inflammation. The invention also relates to methods for identifying products which are useful in therapy, particularly in the treatment of diseases associated with inflammation.

BACKGROUND TO THE INVENTION

The integrins comprise a large family of heterodimeric transmembrane receptors that mediate both cell-cell and cell-matrix interactions. They engage numerous ligands and regulate a variety of cellular and physiological processes such as cell proliferation, apoptosis, migration, differentiation, inflammation and tissue remodelling. The α4β1 integrin is expressed mainly on leukocytes but is also found on smooth muscle cells and tumor cells. It has received particular attention because of its putative role in modulating the inflammatory response, promoting the exfiltration of leukocytes from the circulation. The α4β7 integrin is also thought to play a role in the inflammatory process.

Osteopontin (OPN) is an RGD containing extracellular matrix protein expressed by a number of cell types including osteoclasts, osteoblasts, macrophages, activated T-cells, smooth muscle cells and epithelial cells. It is present in several tissues including bone, kidney, placenta, smooth muscle and secretory epithelia and is associated with normal tissue remodelling processes such as bone resorption, angiogenesis, wound healing and tissue injury as well as certain diseases including restenosis, atherosclerosis, renal diseases and tumorigenesis. Upon infection and damage OPN expression is rapidly upregulated by T cells and macrophages. It acts as a chemoattractant for smooth muscle cells, and may facilitate further recruitment and activation of both T-cells and macrophages. In addition it may also act as a costimulatory molecule for T-cells. The diverse functions of osteopontin suggest that it may be important in both the immune-response and tissue remodelling.

OPN exerts many of its biological effects by interacting with integrins. It constutively binds αvβ3, αvβ5, αvβ1 and α8β1 via a central RGD motif, while proteolytic modification of OPN by thrombin cleavage at aa168 reveals cryptic binding sites for α9β1 and α5β1.

SUMMARY OF THE INVENTION

This invention is based on the finding that α4 integrins bind the extracellular matrix protein osteopontin (OPN) and on the identification of two novel peptide sequences within OPN which bind the α4 integrins α4β1 and α4β7. The importance of an interaction between OPN and α4 integrins is that it provides a link between these proteins, immuno-modulation and inflammatory diseases. Thus the interaction between OPN and α4 integrins, such as α4β1 and α4β7, is an important target for the identification of products which may be used as immuno-modulators or used in the treatment of inflammatory disease.

In order to bind an α4 integrin, the second motif typically needs a free acidic carboxyl terminus. Proteolytic cleavage of OPN at amino acid 168 probably generates this in vivo. In the present invention embodiments using polypeptides with the second motif or functional variants of it will typically have either the free carboxylic acid terminus already present or will able to be cleaved, preferably proteolytically, to give rise to such an acidic group.

According to the present invention there is thus provided a method for a method for identifying a product which is capable of disrupting an interaction between amino acids 136 to 142 and/or amino acids 162 to 168 of human osteopontin (OPN) and an α4 integrin, which method comprises:

(i) providing, as a first component, a polypeptide which is
  (a) up to 50 amino acids in length and which comprises the amino acid sequence $X_1X_2FPTDLPAX_3X_4$ (SEQ ID NO: 2) or a functional variant thereof and/or the amino acid sequence $X_7X_6X_5SVVYGLR$ (SEQ ID NO: 3) or a functional variant thereof or (b) a fusion protein wherein the polypeptide (a) is fused to a carrier polypeptide, wherein:
  $X_1$ is absent or any amino acid and, if $X_1$ is present, $X_2$ is absent or any amino acid;
  $X_3$ is absent or any amino acid and, if $X_3$ is present, $X_4$ is absent or any amino acid; and
  $X_5$ is absent or any amino acid and, if $X_5$ is present, $X_6$ is absent or any amino acid and, if $X_6$ is present, $X_7$ is absent or any amino acid;
(ii) providing, as a second component, an α4 integrin or a functional variant thereof;
(iii) contacting the two components with a test product under conditions that would permit the two components to interact in the absence of the test product; and
(iv) determining whether the test product is capable of disrupting the interaction between the first and second components.

Typically the α4 integrin used as a second component is α4β1.

The invention also provides:
a method for identifying a product which is capable of binding to amino acids 136 to 142 and/or amino acids 162 to 168 of human OPN, which method comprises:

(i) providing, as a first component, a polypeptide which is
  (a) up to 50 amino acids in length and which comprises the amino acid sequence $X_1X_2FPTDLPAX_3X_4$ (SEQ ID NO: 2) or a functional variant thereof and/or the amino acid sequence $X_7X_6X_5SVVYGLR$ (SEQ ID NO: 3) or a functional variant thereof or (b) a fusion protein wherein the polypeptide (a) is fused to a carrier polypeptide, wherein:
  $X_1$ is absent or any amino acid and, if $X_1$ is present, $X_2$ is absent or any amino acid;
  $X_3$ is absent or any amino acid and, if $X_3$ is present, $X_4$ is absent or any amino acid; and
  $X_5$ is absent or any amino acid and if $X_5$ is present, $X_6$ is absent or any amino acid and, if $X_6$ is present, $X_7$ is absent or any amino acid;
(ii) contacting the first component with a test product under conditions that, in the presence of an α4 integrin but the absence of the test product, would lead to an interaction between the first component and an α4 integrin; and
(iii) determining whether the test product is capable of binding to the first component;

a test kit suitable for use in identifying a product which is capable of disrupting an interaction between amino acids 136 to 142 and/or amino acids 162 to 168 of human OPN an α4 integrin, which kit comprises:
(a) a first component as defined above; and
(b) an α4 integrin or a functional variant thereof;
a test kit suitable for identifying a product which is capable of binding to amino acids 136 to 142 and/or amino acids 162 to 168 of human OPN, which kit comprises:

(a) a first component as defined above; and
(b) means for identifying whether a test product binds to the said first component.

a product identified by a method of the invention ("a product of the invention");

a product of the invention for use in a method of treatment of the human or animal body by therapy;

use of a product of the invention in the manufacture of a medicament for use in immuno-modulation or the treatment of an inflammatory disease, a granulomatous disease, fibrotic disease, multiple sclerosis or a bacterial or viral infection;

a pharmaceutical composition comprising a pharmaceutically acceptable carrier or diluent and, as active ingredient, a product of the invention;

a method for treating a host requiring immuno-modulation or suffering from an inflammatory disease, a granulomatous disease, fibrotic disease, multiple sclerosis or a bacterial or viral infection which method comprises administering to the host an effective amount of a product of the invention;

a polypeptide (a) or (b) as defined in relation to a method of the invention, excluding the polypeptide SVVYGLR (SEQ ID NO: 4);

an antibody capable of binding a polypeptide (a) or (b) ("an antibody of the invention");

a polypeptide (a) or (b) or an antibody of the invention; for use in a method of treatment of the human or animal body by therapy;

use of a polypeptide (a) or (b) or an antibody of the invention, in the manufacture of a medicament for use in immuno-modulation or the treatment of an inflammatory disease, a granulomatous disease, fibrotic disease, multiple sclerosis or a bacterial or viral infection;

a pharmaceutical composition comprising a pharmaceutically acceptable carrier or diluent and, as active ingredient, a polypeptide (a) or (b) as defined in a method of the invention, or an antibody of the invention; and a method for treating a host requiring immuno-modulation or suffering from an inflammatory disease, a granulomatous disease, fibrotic disease, multiple sclerosis or a bacterial or viral infection, which method comprises administering to the host an effective amount of a polypeptide (a) or (b) or an antibody of the invention;

use of a polypeptide (a) or (b) in a method for identifying a product which is capable of disrupting an interaction between amino acids 136 to 142 and/or amino acids 162 to 168 of human OPN and an α4 integrin;

use of a polypeptide (a) or (b) in a method for identifying a product which is capable of binding to amino acids 136 to 142 and/or amino acids 162 to 168 of human OPN; and a method of diagnosis of an inflammatory disease, a granulomatous disease, fibrotic disease, multiple sclerosis or a bacterial or viral infection which method comprises contacting an antibody of the invention with a biological sample from a human or animal subject and determining whether the antibody binds to amino acids 136 to 142 and/or amino acids 162 to 168 of OPN, thereby to determine the disease state of the subject.

BRIEF DESCRIPTION OF THE FIGURES

FIG. 2 shows that J6 and HL60 cells adhere to OPN via α4β1. (A) J6 cells were allowed to adhere to wells coated with a GST fusion protein representing intact osteopontin (aa17-314) at 20 µg/ml. Cells were incubated for 35 minutes at 37° C. in the presence of or absence of various function blocking anti-integrin antibodies at 10 µg/ml. To prebind the antibodies cells were preincubated on ice for 10 minutes before being moved to 37° C. Each data point represents the mean±SD of duplicate points. (B) HL60 cells were allowed to adhere to wells coated with a GST fusion protein representing intact osteopontin (aa17-314) at 20 µg/ml. To stimulate α4β1 binding to OPN, 50 ng/ml TPA was also included. Cells were incubated for 35 minutes at 37° C. in the presence or absence of various function blocking anti-integrin antibodies at 10 µg/ml. To prebind the antibodies cells were preincubated on ice for 10 minutes before being moved to 37° C. Each data point represents the mean±SD of duplicate points.

FIG. 3 shows that α4β1 binds within the N-terminal fragment of OPN generated by thrombin cleavage. J6 cells were allowed to attach to wells coated with various concentrations of GST-fusion proteins of intact OPN (aa17-314), thrombin cleaved OPN (aa17-168) and a OPN fragment truncated past the RGD motif (aa17-115) as well as GST fusions of the CS-1 region of fibronectin (CS-1), and repeats 8-10 of fibronectin (FN8-10). Cells were incubated for 35 minutes at 37° C. in the presence (closed circles) or absence (open circles) of the small molecule inhibitor of α4β1, BIO1211, at 100 nM. Each data point represents the mean±SD of duplicate points.

FIG. 4 shows that α4β1 binds a site within aa125-168 distinct from the RGD motif. (A) J6 cells were allowed to attach to wells coated with various concentrations of GST-fusion proteins of OPN aa115-168 and aa125-168 which represent two fragments of thrombin cleaved OPN differentially truncated from the N-terminus. Cells were incubated for 35 minutes at 37° C. in the presence (closed circles) or absence (open circles) of the small molecule inhibitor of α4β1, BIO1211, at 100 nM. Each data point represents the mean±SD of duplicate points. (13) J6 cells were allowed to attach to wells coated with various concentrations of a GST-fusion protein of thrombin cleaved OPN in which the RGD motif is mutated to RAD (aa17-168RAD). Cells were incubated for 35 minutes at 37° C. in the presence (closed circles) or absence (open circles) of the small molecule inhibitor of α4β1, BIO1211, at 100 nM. Each data point represents the mean±SD of duplicate points.

FIG. 5 shows the definition of α4β1 interacting peptides within OPN. (A) The region containing the α4β1 binding site, aa125-168, was divided into 5 overlapping peptides which were expressed as GST fusion proteins. The two peptides which supported α4β1 dependent adhesion are shown in bold. (B) J6 cells were allowed to attach to overlapping GST fusion proteins spanning aa125-168 as shown in (A). All fusion proteins were coated at 20 µg/ml and J6 cells were incubated at 37° C. for 35 minutes. Each data point represents the mean±SD of duplicate points. (C) J6 cells were allowed to attach to wells coated with GST-fusion proteins of OPN aa132-146 and aa153-168, as well as GST-CS-1. Cells were incubated for 35 minutes at 37° C. in the presence (dark grey) or absence (light grey) of 100 nM of the small molecule inhibitor of α1, BIO1211. Each data point represents the mean±SD of duplicate points.

FIG. 6 shows an alignment of the α4β1 binding region, aa125-168. The human, bovine, pig, rabbit, rat and mouse sequences incorporating the α4β1 interacting peptides, aa125-168 are shown. The region identified within the human protein as α4β1 interacting peptides are underlined.

DESCRIPTION OF SEQUENCE LISTING

Figure 1:
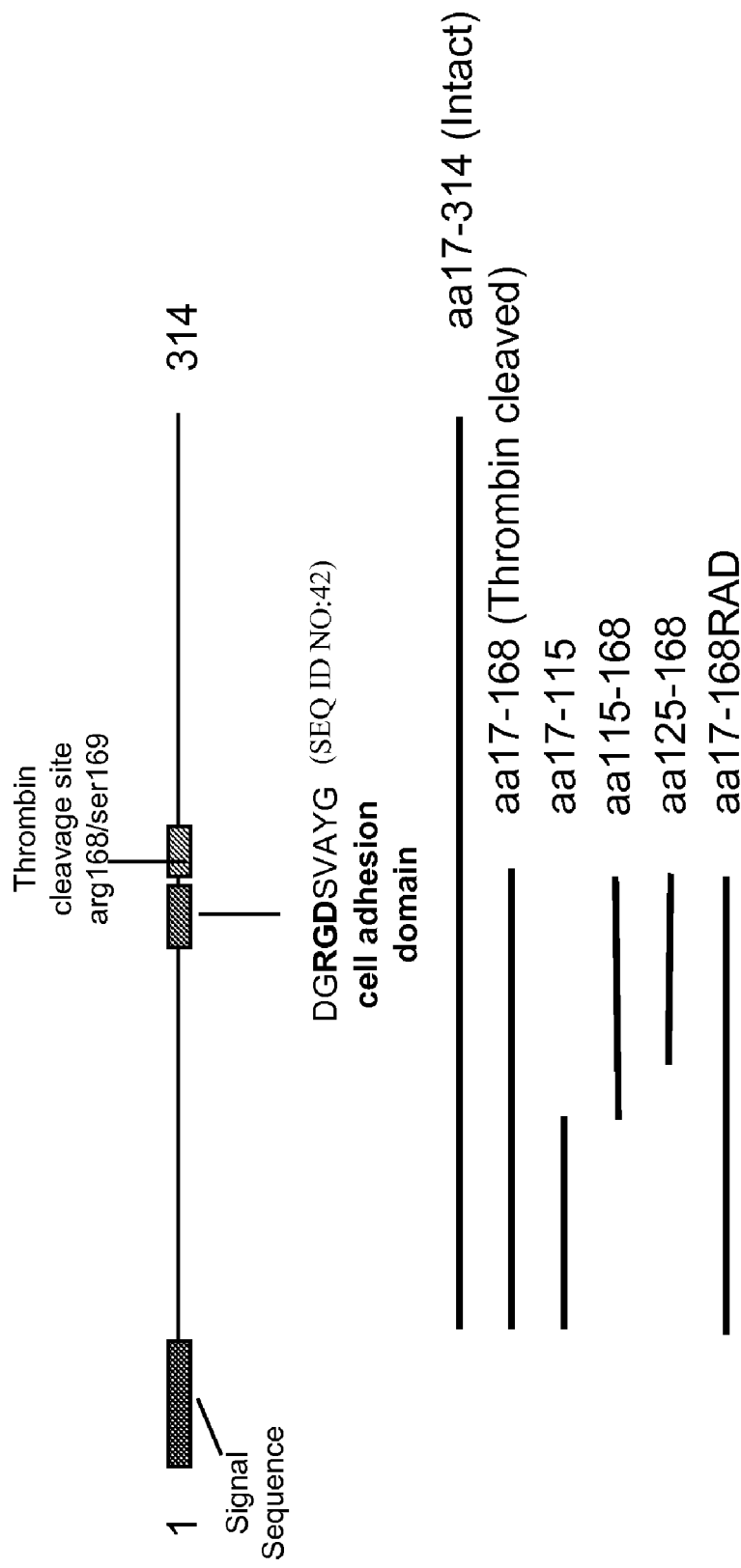
FIG. 1 shows a schematic diagram of the recombinant OPN GST-fusion proteins used for adhesion assays. All OPN fusion proteins were expressed in the lon protease deficient bacterial strain UT5600. Each protein preparation was over 95% pure as judged by mass spectrometry and SDS-PAGE analysis and not subject to protease digestion. The fusion protein aa17-314 represents full length OPN. The fusion protein aa17-168 represents the thrombin cleaved fragment, mimicking proteolytic cleavage with thrombin at amino acid residue 168. The fusion protein aa17-115 represents a further deletion from the C-terminus of OPN past the RGD motif. The two fusion proteins aa115-168 and aa125-168 represent deletions from the N-terminus of the thrombin cleaved fragment. The fusion protein aa17-168RAD represents the thrombin cleaved fragment of OPN in which the RGD motif has been mutated to RAD.

SEQ ID NO: 1 shows the amino acid sequence of human osteopontin (GenBank Accession Number: X13694).

DETAILED DESCRIPTION OF THE INVENTION

We have shown that two new peptide motifs in OPN determine its ability to interact with α4 integrins. The interaction between osteopontin (OPN) and α4 integrins appears to be important in, for example, immuno-modulation, in inflammatory disease and in granulomatous disease and in fibrotic disease and multiple sclerosis. Thus, disruption of the interaction between the new OPN motifs and α4 integrins offers a target for therapy by immuno-modulation and therapy of various types of diseases. One of the motifs comprises amino acids 136 to 142 of OPN and the other comprises amino acids 162 to 168 of OPN.

The motif comprising amino acids 162 to 168 of OPN has a higher affinity for α4 integrins than the motif comprising amino acids 136 to 142 of OPN. The motif comprising amino acids 162 to 168 has its highest affinity for OPN when it has a free carboxyl group (carboxylic acid) at amino acid residue 168. It is likely that in vivo such a free carboxyl group will be present after proteolytic cleavage of OPN at amino acid 168. In embodiments of the invention which use polypeptides carrying the second motif, or a functional variant thereof, the polypeptide will either have such an acidic carboxyl group or will be able to be cleaved to give rise to such a group.

The invention provides methods for identifying a product capable of disrupting an interaction between amino acids 136 to 142 and/or amino acids 162 to 168 of OPN, typically human OPN, and an α4 integrin.

A two component system is used. The two components are contacted in the presence of a test product. The contacting step is typically carried out under conditions that would permit the interaction of the two components being tested in the absence of the test product. The degree of interaction between the two components may be determined so that the degree of disruption of the interaction by the test substance can be determined.

The first component can be a polypeptide (a) which is typically up to about 50 amino acids in length and which comprises the amino acid sequence $X_2X_1FPTDLPAX_3X_4$ (SEQ ID NO: 2) or a functional variant thereof and/or the amino acid sequence $X_7X_6X_5SVVYGLR$ (SEQ ID NO: 3) or a functional variant thereof, wherein:

$X_1$ may be absent or any amino acid and, if present, it is preferably D. If $X_1$ is present, $X_2$ may be absent or any amino acid and, if $X_2$ is present, it is preferably T. Preferably, $X_1$ and $X_2$ are both present and $X_1$ is D and $X_2$ is T.

$X_3$ may be absent or any amino acid and, if present, it is preferably T. If $X_3$ is present, $X_4$ may be absent or any amino acid and, if $X_4$ is present, it is preferably E. Preferably $X_3$ and $X_4$ and both present and $X_3$ is T and $X_4$ is E.

$X_5$ may be absent or any amino acid and, if present, it is preferably D. If $X_5$ is present, $X_6$ may be absent or any amino acid and, if $X_6$ is present, it is preferably G or A. If $X_6$ is present, $X_7$ may be absent or any amino acid and, if $X_7$ is present, it is preferably R. Preferably, $X_5$, $X_6$ and $X_7$ are all present and $X_5$ is D, $X_6$ is G or A and $X_7$ is R.

Thus, the polypeptide (a) is typically a polypeptide which is up to about 50 amino acids in length and comprises the sequence FPTDLPA (SEQ ID NO: 6), DFPTDLPA (SEQ ID NO: 8), TDFPTDLPA (SEQ ID NO: 9), FPTDLPAT (SEQ ID NO: 10), FPTDLPATE (SEQ ID NO: 18), DFPTDLPAT (SEQ ID NO: 12), DFPTDLPATE (SEQ ID NO: 13), TDFPTDLPAT (SEQ ID NO: 14) or TDFPTDLPATE (SEQ ID NO: 15) or functional variants of any thereof and/or SVVYGL (SEQ ID NO: 4), DSVVYGLR (SEQ ID NO: 16), GDSVVYGLR (SEQ ID NO: 17), RGDSVVYGLR (SEQ ID NO: 41) or RADSVVYGLR (SEQ ID NO: 19) or functional variants of any thereof. Alternatively, the polypeptide (a) may consist essentially of an above mentioned amino acid sequence or a functional variant thereof. The polypeptide (a) can comprise or consist essential of both $X_2X_1$FPTDLPAX$_3$X$_4$ (SEQ ID NO: 2) and $X_7X_6X_5$SVVYGLR (SEQ ID NO: 3) or functional variants thereof.

A polypeptide (a) may comprise a functional variant of $X_2X_1$FPTDLPAX$_3$X$_4$ (SEQ ID NO: 2) and/or $X_7X_6X_5$SVVYGLR (SEQ ID NO: 3). A functional variant is a sequence which is similar to $X_2X_1$FPTDLPAX$_3$X$_4$ (SEQ ID NO: 2) or $X_7X_6X_5$SVVYGLR (SEQ ID NO: 3) and which retains α4 integrin binding activity, typically it will retain α4β1 binding activity. Typically, the binding activity of a functional variant may be substantially the same as the binding activity of $X_2X_1$FPTDLPAX$_3$X$_4$ (SEQ ID NO: 2) or $X_7X_6X_5$SVVYGLR (SEQ ID NO: 3). Alternatively, the binding activity of a functional variant may be greater or less than that of one of $X_2X_1$FPTDLPAX$_3$X$_4$ (SEQ ID NO: 2) or $X_7X_6X_5$SVVYGLR (SEQ ID NO: 3). A functional variant typically comprises a sequence substantially similar to $X_2X_1$FPTDLPAX$_3$X$_4$ (SEQ ID NO: 2) or $X_7X_6X_5$SVVYGLR (SEQ ID NO: 3).

A functional variant may have increased or decreased affinity for a particular α4 integrin relative to the wild type OPN motif. For example, the variant may have an increased affinity for α4β1 or α4β7 integrin.

The functional variant may have increased affinity for one α4 integrin but have decreased affinity for a second α4 integrin. For example, the variant may have increased affinity for α4β1 but have decreased affinity for α4β7 or vice versa. Such variants may be used as therapeutic molecules to selectively act against a particular α4 integrin without affecting the other α4 integrin. Typically these variants will have amino acid changes in, or around, the binding motif or in a region affecting its activity. In particular such variants may have different amino acids at the amino acid positions corresponding to amino acid residues 166 and/or 168 of the wild type OPN binding site.

Thus a functional variant will generally have at least 60%, at least 70%, at least 80%, at least 90%, at least 95%, at least 98 or at least 99% sequence identity to $X_2X_1$FPTDLPAX$_3$X$_4$ (SEQ ID NO: 2) or $X_7X_6X_5$SVVYGLR (SEQ ID NO: 3), calculated over the full length of those sequences. The UWGCG Package provides the BESTFIT program which can be used to calculate identity (for example used on its default settings) (Devereux et al (1984) *Nucleic Acids Research* 12, p387-395). The PILEUP and BLAST algorithms can be used to calculate identity or line up sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Centre for Biotechnology Information (www.ncbi.nlm.nih.gov/).

A functional variant may be a naturally occurring sequence, for example an allelic variant. An allelic variant will generally be of human or non-human mammal, for example bovine or porcine, origin.

Alternatively, a functional variant may be a non-naturally occurring sequence. A non-naturally occurring functional variant may be a modified version of $X_2X_1$FPTDLPAX$_3$X$_4$ (SEQ ID NO: 2) or $X_7X_6X_5$SVVYGLR (SEQ ID NO: 3) obtained by, for example, amino acid substitution or deletion. 1, 2, 3, 4 or 5 amino acid substitutions or deletions may be made. Typically, the substitutions will be conservative substitutions, for example according to the following Table. Amino acids in the same block in the second column and preferably in the same line in the third column may be substituted for each other. Deletions are preferably deletions of amino acids from one or both ends of the sequences given in SEQ ID NOS: 1 and 2.

| ALIPHATIC | Non-polar | G, A, P |
| --- | --- | --- |
| | | I, L, V |
| | Polar-uncharged | C, S, T, M |
| | | N, Q |
| | Polar-charged | D, E |
| | | K, R |
| AROMATIC | | H, F, W, Y |

Functional variants may be sequences intermediate between human and non-human alleles. For example, the bovine version of the human $X_2X_1$FPTDLPAX$_3$X$_4$ (SEQ ID NO: 2), motif is $X_2X_1$FPTDIPTX$_3$X$_4$ (SEQ ID NO: 20), and a functional variant may contain one or both differences between the human and bovine sequence. Thus, a functional variant may be $X_2X_1$FPTDX$_a$PX$_b$X$_3$X$_4$ (SEQ ID NO: 21), wherein $X_a$ is L or I and $X_b$ is A or T. Similarly, the bovine version of the human motif $X_7X_6X_5$SVVYGLR (SEQ ID NO: 3) is $X_7X_6X_5$SVAYGLK (SEQ ID NO: 22) and thus, a functional variant may be $X_7X_6X_5$SVX$_c$YGLX$_d$ (SEQ ID NO: 23), wherein $X_c$ is V or A and $X_d$ is R or K.

A polypeptide (a) is typically up a longer polypeptide of to about 50 amino acids in length. Thus, a polypeptide (a) may have the sequence:

(1) $(X_{aa})_m X_2 X_1$FPTDLPAX$_3$X$_4(X_{aa})_n$ (SEQ ID NO: 11) or a functional variant thereof, wherein $X_1$ to $X_4$ are present, n is 0 to 39 such as 5 to 25, m is 0 to 39 such as 5 to 25, (m+n) is 0 to 39 and any $X_{aa}$ is independently any amino acid; or (2) $(X_{aa})_p X_7 X_6 X_5$SVVYGLR (SEQ ID NO: 54) or a functional variant thereof, wherein $X_5$ to $X_7$ are present, p is 0 to 40 such as 5 to 25 and $X_{aa}$ is independently any amino acid.

Put another way, the motif FPTDLPA (SEQ ID NO: 6) or a functional variant thereof may be extended by the addition of from 1 to about 43 amino acids, for example from 5 to 25 amino acids, and the motif SVVYGLR (SEQ ID NO: 4) may be extended by the addition of from 1 to about 43 amino acids, for example from 5 to 25 amino acids.

The OPN motif comprising amino acids 136 to 142 of OPN, or a functional variant of this motif, may be situated at any point of a polypeptide which is up to about 50 amino acids in length. For example, this OPN motif may be situated at the C- or N-terminal end of a polypeptide. Generally, however, the OPN motif will be situated substantially in the centre of a polypeptide, i.e. m and n are typically a similar integer.

The binding motif comprising amino acids 162 to 168 of OPN, or a functional variant thereof, will typically be present at the C-terminus of the polypeptide (a). The polypeptide (a) may have amino acid residues C terminal to the motif, however if this is the case these will typically be removed at some stage by proteolytic cleavage prior to binding to the α4 integrin.

The flanking sequences (i.e. those represented by $X_{aa}$ in the formulae above) may be of any suitable sequence. However, the flanking sequences should be such that interaction between the OPN motif and the α4 integrin can occur. Thus, the flanking sequences allow the OPN motif to adopt an appropriate conformation for binding to the α4 integrin and will be capable of presenting the motif. It can be easily determined whether the motif is presented by determining whether the polypeptide comprising the motif is capable of binding to an α4 integrin. In addition, the flanking sequences typically should substantially not interact with the α4 integrin.

Preferably, the flanking sequences are the same or substantially similar to the sequences that flank the OPN motifs in the wild type human OPN polypeptide or are functional variants thereof. For example, a polypeptide (a) may comprise the sequence defined by amino acids 132 to 142, 136 to 146 or 132 to 146 and/or 156 to 148 of SEQ ID NO: 1 or a functional derivative thereof. Indeed, polypeptides that comprise human OPN flanking sequences are preferred as they may provide for increased binding to an α4 integrin.

Therefore:

$(X_{aa})_m$ may be V, LV, ELV, DELV (SEQ ID NO: 55), SDELV (SEQ ID NO: 56), ESDELV (SEQ ID NO: 57), DESDELV (SEQ ID NO: 58), SDESDELV (SEQ ID NO: 59), HSDESDELV (SEQ ID NO: 60) or HHSDESDELV (SEQ ID NO: 61) etc. or functional variants thereof, for example;

$(X_{aa})_n$ may be V, VF, VFT, VFTP (SEQ ID NO: 62), VFTPV (SEQ ID NO: 63), VFTPVV (SEQ ID NO: 64), VFTPVVP (SEQ ID NO: 65), VFTPVVPT (SEQ ID NO: 66), VFTPVVPTV (SEQ ID NO: 67) or VFTPVVPTVD (SEQ ID NO: 68) etc. or functional variants thereof, for example;

$(X_{aa})_p$ may be D, YD, TYD, DTYD (SEQ ID NO: 69), VDTYD (SEQ ID NO: 70), TVDTYD (SEQ ID NO: 71), PTVDTYD (SEQ ID NO: 72), VPTVDTYD (SEQ ID NO: 73), VVPTVDTYD (SEQ ID NO: 74), or PVVPTVDTYD (SEQ ID NO: 75) etc. or functional variants thereof, for example; and $(X_{aa})_q$ may be S, SK, SKS, SKSK (SEQ ID NO: 76), SKSKK (SEQ ID NO: 77), SKSKKF (SEQ ID NO: 78), SKSKKFR (SEQ ID NO: 79), SKSKKFRR (SEQ ID NO: 80), SKSKKFRRP (SEQ ID NO: 81) or SKSKKFRRPD (SEQ ID NO: 82) etc. or functional variants thereof, for example.

Preferred polypeptides (a) comprise both OPN motifs. The two motifs may be placed adjacent to each other with no intervening sequences. However, typically a sequence will intervene between the two motifs. A preferred intervening sequence is one which is substantially similar to the sequence of amino acids 143 to 157 of the human OPN sequence or a functional variant thereof. Polypeptides which comprise both motifs may be useful if high affinity binding to an α4 integrin requires both OPN motifs.

Polypeptides (b) for use in the invention comprise a polypeptide (a) fused to a carrier polypeptide. Additional amino acid residues may be provided at one or both termini of a polypeptide (a) for the purpose of providing a carrier polypeptide, by which the polypeptide can be, for example, affixed to a label, solid matrix or carrier. Thus the polypeptide (b) may be in the form of a fusion polypeptide which comprises heterologous sequences. Indeed, in practice it may often be convenient to use fusion polypeptides. This is because fusion polypeptides may be easily and cheaply produced in recombinant cell lines, for example recombinant bacterial or insect cell lines. Typically fusion polypeptides will comprise a polypeptide sequence as described above and a carrier or linker sequence. The carrier or linker sequence will typically be derived from a non-human, preferably a non-mammalian source, for example a bacterial source. This is to minimize the occurrence of non-specific interactions between sequences in the fusion polypeptide and the α4 integrin.

In the case of fusion proteins comprising the SVVYGLR (SEQ ID NO: 4) motif, or a functional variant thereof, amino acids C-terminal to the arginine residue will typically be removed by proteolytic cleavage prior to binding to an α4 integrin.

Polypeptides may be modified by, for example, addition of histidine residues, a T7 tag or glutathione S-transferase, to assist their purification. Alternatively, the carrier polypeptide may promoter secretion of the polypeptide from a cell or target expression of the polypeptide to a particular subcellular compartment. Amino acids carriers can be from 1 to 400 amino acids in length or more typically from 5 to 200 residues in length. The polypeptide may be linked to a carrier polypeptide directly or via an intervening linker sequence. Typical amino acid residues used for linking are tyrosine, cysteine, lysine, glutamic acid or aspartic acid.

Suitable polypeptides for use as a first component may be chemically modified, for example, post translationally modified. For example they may be glycosylated or comprise modified amino acid residues. Polypeptides can be in a variety of forms of polypeptide derivatives, including amides and conjugates with polypeptides.

Chemically modified polypeptides also include those having one or more residues chemically derivatized by reaction of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine.

Also included as chemically modified polypeptides are those polypeptides which contain one or more naturally occurring amino acids derivatives of the twenty standard amino acids. For example, 4-hydroxyproline may be substituted for proline or homoserine may be substituted for serine.

Polypeptides may carry a revealing label. Suitable labels include radioisotopes such as $^{32}P$ or $^{35}S$, fluorescent labels, enzyme labels, or other protein labels such as biotin.

Polypeptides may be expressed using recombinant DNA techniques. For example, suitable polypeptides may be expressed in, for example, bacterial or insect cell lines.

Alternatively, polypeptides may be chemically synthesized. The upper limit for a chemically synthesized polypeptide is typically about 50 amino acids. Synthetic techniques, such as a solid-phase Merrifield-type synthesis, may be preferred for reasons of purity, antigenic specificity, freedom from unwanted side products and ease of production. Suitable techniques for solid-phase peptide synthesis are well known to those skilled in the art (see for example, Merrifield et al., 1969, Adv. Enzymol 32, 221-96 and Fields et al., 1990, Int. J. Peptide Protein Res, 35, 161-214). In general, solid-phase synthesis methods comprise the sequential addition of one or more amino acid residues or suitably protected amino acid residues to a growing peptide chain.

Polypeptides for use as a first component in a method of the invention may be linear or cyclic. A linear polypeptide may be cyclised according to any suitable method (see for example Zimmer et al., 1992, Peptides, pp.393-394, ESCOM Science Publishers, BV., 1993 and Gurrath et al., 1992, Eur. J. Biochem., 210, 911-921). Typically, tertbutoxycarbonyl protected polypeptide methyl ester is dissolved in methanol and sodium hydroxide are added and the admixture is reacted at 20° C. to hydrolytically remove the methyl ester protecting group. After evaporating the solvent, the tertbutoxycarbonyl protecting group is extracted with ethyl acetate from acidified aqueous solvent. The tertbutoxycarbonyl protecting group is then removed under mildly acidic conditions in dioxane cosolvent. The unprotected linear peptide with free amino acid and carboxy termini so obtained is converted to its corresponding cyclic polypeptide by reacting a dilute solution of the linear polypeptide in a mixture of dimethylformamide with dicyclohexylcarboiimide in the presence of 1-hydroxy benzotriazole and N-methylmorpholine. The resultant cyclic polypeptide is purified by chromatography.

The second component comprises an α4 integrin or a functional variant thereof. The α4 integrin family comprises α4β1 and α4β7 integrins and either of these, or a function variant thereof, may be used in the invention. Typically α4β1 may be used.

A functional variant of an α4 integrin is a polypeptide which shows α4 integrin-like activity in respect of the ability of α4 integrins to bind OPN. More specifically, the functional variant is able to bind at least one of the amino acid motifs represented by 136 to 142 and amino acids 162 to 168 of OPN. Thus, the second component may comprise, for example, a fragment of an α4 integrin which binds amino acids 136 to 142 and/or amino acids 162 to 168 of OPN, or a polypeptide which comprises wild type sequences for OPN binding sites and elsewhere comprises non-wild type sequences. Preferably the variant will be able to bind the amino acid motif represented by amino acids 162 to 168 of OPN.

Also, suitable functional variants may comprise non-wild type OPN binding sites, but will still be capable of binding at least one of the amino acid motifs represented by 136 to 142 and amino acids 162 to 168 of OPN and preferably the amino acid motif represented by amino acids 162 to 168 of OPN. It may be preferable to use non-wild type binding sites which show an increased binding affinity for those motifs, as compared with the binding affinity of wild type binding sites. Use of such non-wild type binding sites may allow the identification of products which are strong disrupters of OPN/α4 integrin interactions. Non-wild type OPN binding sequences will typically arise through substitution or deletion for example, as described for the first component above.

Second component polypeptides may be produced according to similar methods as described for first component polypeptides.

A two component assay can be carried out according to any suitable protocol, but preferably the assay is adapted so that it can be carried out in a single reaction vessel and more preferably can be carried out in a single well of a plastics microtitre plate and thus can be adapted for high through-put screening. Typically, a cell adhesion assay is carried out.

In a cell adhesion assay, the first component polypeptide is coated on the walls of a suitable vessel, in particular the well of a plastics microtitre plate. In one suitable assay format, the second component, produced, for example, chemically or recombinantly is simply added to the assay vessel. Binding of the second component to the first component can be followed by the use of a second component which carries a label, for example a radioactive label or a fluorescent label.

Alternatively, in another suitable assay format, cells expressing the second component are added to the vessel and allowed to interact with the first component in the presence of a test product. The number of cells which bind to the first component polypeptide is then determined. This may be carried out by, for example, staining the cells and then carrying out spectrophotometry. It may be necessary to add further components to the reaction mixture in order to promote the α4 integrin to a suitable activation state for binding to OPN. In addition, suitable control experiments may be carried out. The cell adhesion assay may be run without the test product present. In order to distinguish between non-specific interactions between the first component and cells expressing the second component, antibodies specific to one of the two polypeptides of the α4 integrin may be added to the reaction mixture. Control cells expressing polypeptides other than the two polypeptides of the α4 integrin may be used, to distinguish between specific reactions between the first and second components and non-specific reactions between the α4 integrin and other surface proteins of the cells expressing the second component.

A product of the invention which disrupts an interaction causes the degree of interaction to be reduced or substantially eliminated as compared to the degree of interaction in the absence of the product. Preferred products cause a reduction in the degree of interaction as compared to that in the absence of the product of at least 10%, at least 20%, at least 30%, at least 40%, at least 50%, at least 60%, at least 70%, at least 80%, at least 90%, at least 95% or at least 99% or substantially eliminate the interaction at a concentration of the product of 0.1 mg ml$^{-1}$, 1 mg ml$^{-1}$, 10 mg ml$^{-1}$, 100 mg ml$^{-1}$, 500 mg ml$^{-1}$, 1 mg ml$^{-1}$, 10 mg ml$^{-1}$, 100 mg ml$^{-1}$ or 0.1 g ml$^{-1}$. Any combination of the above percentage reductions in the degree of interaction and concentrations of product may be used to define a product of the invention, with greater disruption at lower concentrations being preferred. Preferred products of the invention are those which show a 50% level of inhibition at a concentration of 1 mg ml$^{-1}$ or 0.5 mg ml$^{-1}$.

The invention also provides a method for identifying a product which is capable of binding to amino acids 136 to 142 and/or amino acids 162 to 168 of OPN. The method comprises contacting a test product with a polypeptide which comprises amino acids 136 to 142 amino acids of OPN or an analogous sequence thereto and/or amino acids 162 to 168 of OPN or an analogous sequence thereto. The ability of the test product to bind to the polypeptide is then determined.

In this type of assay the polypeptide may be the same as the first component described above for a two component assay. Any suitable assay format may be used. Again, protocols which can be adapted for use in high through-put screens are preferred.

Any substance may be used as a test product. Suitable test products include combinatorial libraries, defined chemical entities, peptides and peptide mimetics, oligonucleotides and natural product libraries, such as display libraries (for example phage display libraries). The test products may be used in an initial screen of, for example, ten products per reaction, and the products of batches which show antagonism tested individually. Furthermore, antibody products (for example, monoclonal and polyclonal antibodies, single chain antibodies, chimeric antibodies, CDR-grafted antibodies and humanised antibodies) or fragments thereof may be used.

It is preferable that products which disrupt the interaction between OPN and an α4 integrin do not disrupt the interaction between OPN and other integrins such as αvβ3, αvβ5, αvβ1 and α8β1. That is, that products are specific for the interaction between OPN and an α4 integrin. It is possible that the new motifs represent motifs unique to the interaction between OPN and α4 integrins and therefore that they represent targets for the specific disruption of the OPN/α4 integrin interaction. This contrasts with the central RGD motif of OPN which determines its ability to bind to a number of integrins including αvβ3, αvβ5, αvβ1 and α8β1.

Suitable products include functional derivatives of α4 integrins, fragments derived from the OPN binding sites of an α4 integrin, mimetics of either an α4 integrin or a natural ligand of an α4 integrin, for example polypeptides based on OPN that mimic the structural region involved in α4 integrin-ligand binding interactions, polypeptides having a sequence corresponding to a functional binding domain of the natural ligand specific for an α4 integrin and antibodies which immunoreact with either the motifs of OPN identified above or the regions of the α4 integrin responsible for those interactions.

Products of the invention may be in substantially purified form. They may be in substantially isolated form, in which case they will generally comprise at least 80% e.g. at least 90, 95, 97 or 99% by weight of the dry mass in the preparation. The product is typically substantially free of other cellular components. The product may be used in such a substantially isolated, purified or free form in the method or be present in such forms in a kit.

Products of the invention may be used in a method of treatment of the human or animal body by therapy. In particular such substances may be used in immuno-modulation or in the treatment of an inflammatory disease, granulomatous disease, fibrotic disease, multiple sclerosis or a bacterial or viral infection. Such substances may also be used for the manufacture of a medicament for use in immuno-modulation or in the treatment of an inflammatory disease, granulomatous disease, fibrotic disease, multiple sclerosis or a bacterial or viral infection. The condition of a patient requiring an α4 integrin can be improved by administration of a product of the invention, typically the patient may require α4β1. A therapeutically effective amount of a product of the invention may be given to a host in need thereof.

Preferably, the products used therapeutically will be those which can modulate the interaction of an α4 integrin with the motif comprising amino acids 162 to 168 of OPN, or a functional variant thereof. The products may also be able to modulate the interaction of an α4 integrin with the motif comprising amino acids 136 to 142 of OPN, or a functional variant thereof.

Examples of inflammatory diseases which may be treated with a product of the invention include asthma, athersclerosis, restenosis, ischaemia/reperfusion injury, arthritis, inflammatory bowel disease, type 1 diabetes, systemic lupus erythematosis or multiple organ dysfunction syndrome associated with trauma and sepsis. Examples of granulomatous disease which may be treated with a product of the invention include tuberculosis and sarcodiosis. An example of a bacterial infection is tuberculosis. An example of a viral infection is influenza.

Products of the invention may be administered in a variety of dosage forms. Thus, they can be administered orally, for example as tablets, troches, lozenges, aqueous or oily suspensions, dispersible powders or granules. The antagonists may also be administered parenterally, either subcutaneously, intravenously, intramuscularly, intrasternally, transdermally or by infusion techniques. The inhibitors may also be administered as suppositories. A physician will be able to determine the required route of administration for each particular patient.

The formulation of a product of the invention will depend upon factors such as the nature of the exact antagonist, whether a pharmaceutical or veterinary use is intended, etc. A product of the invention may be formulated for simultaneous, separate or sequential use.

A product of the invention is typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they maybe in the form of sterile, aqueous, isotonic saline solutions.

A therapeutically effective amount of product of the invention is administered to a patient. The doses of a product of the invention may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg of body weight, according to the activity of the specific inhibitor, the age, weight and conditions of the subject to be treated, the type and severity of the degeneration and the frequency and route of administration. Preferably, daily dosage levels are from 5 mg to 2 g.

The invention also provides a polypeptide which is (a) up to 50 amino acids in length and which comprises the amino acid sequence $X_2X_1FPTDLPAX_3X_4$ (SEQ ID NO: 2), or a functional variant thereof and/or the amino acid sequence $X_7X_6X_5SVVYGLR$ (SEQ ID NO: 3) or a functional variant thereof or (b) a fusion protein wherein the polypeptide in (a) is fused to a carrier polypeptide, wherein:

X$_1$ is absent or any amino acid and, if X$_1$ is present, X$_2$ is absent or any amino acid;

X$_3$ is absent or any amino acid and, if X$_3$ is present, X$_4$ is absent or any amino acid; and X$_5$ is absent or any amino acid and, if X$_5$ is present, X$_6$ is absent or any amino acid and, if X$_6$ is present, X$_7$ is absent or any amino acid;

excluding the polypeptide consisting essentially of the sequence SVVYGLR (SEQ ID NO: 4).

Polypeptides (a) and (b), functional variants thereof and methods for producing such polypeptides and functional variants are described in detail above.

Polypeptides (a) and (b) and functional variants thereof may be used in a method for the identification of products which are capable of disrupting an interaction between amino acids 136 to 142 and/or amino acids 162 to 168 of human OPN and an α4 integrin or in a method for the identification of a product which is capable of binding to amino acids 136 to 142 and/or amino acids 162 to 168 of human OPN and an α4 integrin. Typically, such methods will be a method as described above. Typically the α4 integrin will be α4β1 or α4β7.

Polypeptides (a) and (b) and functional variants thereof can also be used in a method of treatment of the human or animal body by therapy. Thus, the said polypeptides may be used in the same way as products of the invention described above and formulated in an identical fashion for the treatment of the medical conditions described above. Cyclic polypeptides may be preferred for use in methods of treatment.

In addition, polypeptides (a) and (b) and functional variants thereof may be used to disrupt the interaction between α4 integrin ligands other than OPN, including VCAM-1, the CS-1 fragment of fibronectin, MAdCAM CS-S, FN-1115, FN-III14 and the disintegrin EC3. In particular they may be used to disrupt the interaction of VCAM-1, the CS-1 fragment of fibronectin, CS-5, FNIII5, FNIII4, VCAM or EC3 with α4β1 or the interaction of α4β7 with VCAM, the CS-1 fragment of fibronectin, CS-5, FN-III5, FNIII4, and MAdCAM.

VCAM is involved in mediating exfiltration of cells from the blood stream and is expressed on the blood vessel wall. CS-1 is a fragment of fibronectin found, as an alternatively spliced region, in areas undergoing active or chronic inflammation. This is found in the tissue rather than on the vessel wall and may influence cell behavior once it has entered the inflamed area. Thus, polypeptide (a) and (b) and functional variants thereof may be used in methods of treatment of conditions in which VCAM, MAdCAM, CS-1, CS-5, FNIII5, FNIII14 and/or EC3 bind to an α4 integrin. Such conditions include those requiring immunomodulation and inflammatory disease, granulomatous disease, fibrotic disease, multiple sclerosis or a bacterial or viral infection. The polypeptides may also be used for the manufacture of a medicament for use in immuno-modulation or in the treatment of an inflammatory disease, granulomatous disease, fibrotic disease, multiple sclerosis or a bacterial or viral infection.

Examples of inflammatory diseases which may be treated with a polypeptide (a) or (b) or a functional variant thereof, include asthma, athersclerosis, restenosis, ischaemia/reperfusion injury, arthritis, inflammatory bowel disease, type 1 diabetes, systemic lupus erythematosis or multiple organ dysfunction syndrome associated with trauma and sepsis. Examples of granulomatous disease which may be treated with a product of the invention include tuberculosis and sarcodiosis. An example of a bacterial infection is tuberculosis. An example of a viral infection is influenza.

Treatment or prevention of some disorders may require the targeting of a specific α4 integrins, for example of α4β1 rater than of α4β7 or vice versa. Accordingly, polypeptides, products or antibodies of the invention which affect the activity of one of the α4 integrins but not the other may be used to treat such disorders.

Polypeptides (a) and (b) and functional variants thereof may be used in structural analysis methods for the design of products which are capable of disrupting the interaction between OPN and an α4 integrin and preferably specifically disrupt the interaction between one of the OPN motifs discussed above and an α4 integrin. Various structural analysis methods for drug-design are known in the art, including, for example, molecular modelling, two-dimensional nuclear magnetic resonance (2-D NMR) analysis and x-ray crystallography.

In order to bind an α4 integrin the SVVYGLR (SEQ ID NO: 4) motif, or functional variants of it, need a free acidic carboxyl terminus. This is normally generated in vivo by cleavage at Arg 168 by thrombin to reveal such a group. The unusual way in which the binding site is generated also provides a target for therapeutic intervention.

Inhibitors which prevent the cleavage by thrombin (or any other protease which carries out the cleavage) may be used to prevent the creation of the SVVYGLR (SEQ ID NO: 4) binding site and hence be used to prevent interaction with α4 integrins and therefore to treat disorders involving these integrins. Such inhibitors may prevent this cleavage in specific α4 integrin ligands rather than all of them and be used to treat disorders in which that specific ligand is involved.

The polypeptides of the invention which carry the SVVYGLR (SEQ ID NO: 4) motif, or functional variant of it, may have a masking group which prevents the acid COOH group of the Arginine interacting with an α4 integrin until the masking group is removed. The unmasking of such polypeptides may be carried out at the local site where the unmasked and hence active polypeptide is required. This enables α4 integrin inhibitors of the specific site it is required.

Computer-based methods which permit the identification of compounds with a desired molecular structure may be used to identify compounds whose structure is similar to all or a part of a compound of interest. Thus, compounds whose structure is similar to the polypeptides of the invention may be identified and such compounds may be capable of disrupting the interaction between OPN and an α4 integrin. Such computer-based methods fall into two-broad classes: database methods and de novo design methods. In database methods the compound of interest is compared to all compounds present in a database of chemical structures and compounds whose structure is in some way similar to the compound of interest are identified. The structures in the database are based either on experimental data, generated by NMR or x-ray crystallography, or modeled three-dimensional structures based on two-dimensional data. In de novo design methods, models of compounds whose structure is in some way similar to the compound of interest are generated by a computer program using information derived from known structures and/or theoretical rules.

The success of both database and de novo methods for identifying compounds with activities similar to the compound of interest depends on the identification of the functionally relevant portion of the compound of interest. For drugs, the functionally relevant portion is referred to as a pharmacophore. A pharmacophore is an arrangement of structural features and functional groups important for biological activity. Thus, pharmacophores may be identified which correspond to polypeptides of the invention. Such pharmacophores may allow the identification of products with a similar structure to polypeptides of the invention and which may be capable of interfering with the interaction between OPN and an α4 integrin.

Programs suitable for generating predicated three-dimensional structures from two-dimensional data include Concord (Tripos Associates, St. Louis, Mo.) and 3-D Builder (Chemical Design Ltd., Oxford, UK). Programs suitable for searching three-dimensional databases to identify molecules bearing a desired pharmacophore include MACCS-3D and ISIS/3D (Molecular Design Ltd., San Leandro, Calif.) and ChemDBS-3D (Chemical Design Ltd., Oxford, UK). Programs suitable for pharmacophore selection and design include DISCO (Abbott Laboratories, Abbott Park, Ill.) and catalyst (Bio-CAD Corp., Mountain view, Calif.). Databases of chemical structures are available from Cambridge Crystallographic Data Centre (Cambridge, UK) and Chemical Abstracts Service (Columbus, Ohio). De novo design programs include Ludi (Biosym Technologies Inc., San Diego, Calif.) and Aladdin (Daylight Chemical Information Systems, Irvine, Calif.). Such programs are well known to those skilled in the art.

The invention also provides monoclonal or polyclonal antibodies capable of binding to a polypeptide (a) or (b) or a functional variant thereof. Typically, such antibodies will bind to a sequence comprising one or both of the motifs FPTDLPA (SEQ ID NO: 6) or SVVYGLR (SEQ ID NO: 4) or functional variants thereof and thus preferred antibodies of the invention are capable of disrupting an interaction between disrupting an interaction between amino acids 136 to 142 and/or amino acids 162 to 168 of OPN and an α4 integrin.

Thus, an antibody of the invention may interact with an amino acid sequence which occurs within the region of OPN defined by amino acid 138 to 168 of SEQ ID NO: 1 or a sequence which is a functional variant thereof. The invention further provides a process for the production of monoclonal or polyclonal antibodies of the invention.

Antibodies of the invention may be antibodies to human polypeptides or fragments thereof. Preferred antibodies are those which are able to discriminate between the two α4 integrin binding site in OPN. That is, preferred antibodies are specific for one of the those binding sites.

For the purposes of this invention, the term "antibody", unless specified to the contrary, includes fragments of whole antibodies which maintain their binding activity for a polypeptide encoded by a polynucleotide of the invention, a polypeptide of the invention or a fragment thereof. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies of the invention may be used, inter alia, in a method of treatment of the human or animal body by therapy. Antibodies may also be used in a method for detecting polypeptides of the invention present in a biological sample, which method comprises:
I providing an antibody of the invention;
II incubating a biological sample with said antibody under conditions which allow for the formation of an antibody-antigen complex; and
III determining whether antibody-antigen complex comprising said antibody is formed.

A sample may be for example a tissue extract. Antibodies of the invention may be bound to a solid support and/or packaged into kits in a suitable container along with suitable reagents, controls, instructions, etc.

The presence of osteopontin in a host may be indicative of a disease state. For example, elevated levels of osteopontin may be indicative of a condition requiring immuno-modulation, an inflammatory disease, granulomatous disease, fibrotic disease, multiple sclerosis or a bacterial or viral infection. Thus antibodies in the invention may be useful in the diagnosis of such conditions. In a method for diagnosis of a condition linked to elevated OPN levels, a sample from a host is contacted with an antibody of the invention. Determining whether the antibody binds to polypeptides in the sample allows evaluation of the disease state of the host. Suitable samples include blood, serum and saliva. Alternatively, antibodies may be linked to a revealing label and thus may be suitable for use in methods of in vivo OPN imaging.

Antibodies of the invention may also be used in a method of treatment of the human or animal body by therapy. They may be used and formulated as is described above for products of the invention. Humanized monoclonal antibodies are preferred for use in methods of treatment and offer particular advantages over murine monoclonal antibodies. Specifically, humanized antibodies are not cleared from the circulation as rapidly as murine antibodies and are not as antigenic as murine antibodies.

Antibodies of the invention can be produced by any suitable method. Means for preparing and characterizing antibodies are well known in the art, see for example Harlow and Lane (1988) "Antibodies: A Laboratory Manual", cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumor cells (Kohler and Milstein (1975) Nature 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunization of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Humanized antibodies may be obtained by replacing components of a non-human antibody with human components, without substantially interfering with the ability of the antibody to bind antigen.

The following Example illustrates the invention:

EXAMPLE

Materials and Methods

Cell Culture

J6, HL60 and RPMI8866 cells were maintained in 1:1 RPMI 1640, Hepes modification (Gibco): Dulbecco's Minimum Essential Medium (DME), Hepes modification (Sigma) supplemented with glutamax (Gibco) and 10% fetal calf serum, FCS.

Antibodies and Other Reagents

Antibody clones used were as follows. The anti-β1 integrin antibody clone 4B4 was obtained from Coulter. The anti-α4 integrin clone HP2/1, anti-α5 integrin clone SAM-1, anti-αL integrin clone 25.3, anti-αm integrin clone Bear1, anti-αv integrin clone AMF7, and anti-β2 integrin clone 7E4 antibodies were obtained from Immunotech. The anti-α9 integrin clone Y9A2, anti-αvβ3 integrin clone LM609 and anti-b6 integrin clone 10D5 antibodies were obtained from Chemicon. The anti-β7 function blocking antibody clone Fib504 was purified in house from a hybridoma obtained from the ATCC. The isotype control (MOPC21) was from Sigma. Phorbol 12-myristate 13-acetate (TPA) was obtained from Sigma. The α4β1 inhibitor BIO1211 (Lin et al, J. Med. Chem. 42, 920-934, 1999) was synthesized in house. All oligonucleotides were obtained from GibcoBRL. Gels for polyacrylamide gel electrophoresis were obtained from Novex.

Flow Cytometry

For FACS analysis approximately $0.5 \times 10^6$ cells were used for each antibody. Cells were washed once in FACS buffer (PBS, 2.5% FCS, 0.1% sodium azide) and then incubated with 1 μg of the relevant antibody for 10 minutes at room temperature. Cells were pelleted and washed two times in FACS buffer, before incubation for a further 10 minutes with anti-mouse IgG Alexa488-conjugated secondary antibody (Molecular Probes). Finally cells were washed again twice in FACS buffer and resuspended in FACS buffer. Cells were analyzed on a Coulter EPICS XL-1 flow cytometer.

Production of Recombinant Protein Fragments

The full length human OPN cDNA (accession number X13694) was cloned by RT-PCR using the Superscript II kit (Stratagene) from kidney poly A+ RNA (Clontech). This cDNA was then used as a template to generate the fragments used in this study. All PCR reactions were performed using Pfu (Stratagene). The fragments encoding intact osteopontin lacking the leader sequence (aa17-314), the thrombin cleaved fragment of osteopontin (aa17-168), a further 53 amino acid residue deletion (aa17-115), aa115-168 and 125-168 were generated by PCR. Each 5' primer incorporated a BamHI site, while each 3' primer incorporated a terminal stop codon and a XbaI site.

The resultant PCR products were first cloned into PCR-script, the sequence verified, then subcloned as a BamHI/XbaI fragment into a modified pGEX-2T vector (a gift from Christine Ellis, GlaxoWellcome). The pGEX-FN8-10 construct (encoding repeats 8-10 of fibronectin) was similarly generated by cloning a HindIII/Sph1 PCR generated fragment into the same modified pGEX-2T vector. The pGEX-CS-1 construct was obtained from Neil Burden (GlaxoWellcome, UK). The short overlapping peptides spanning aa125-168 were constructed by annealing complementary oligos and ligating into the BamH1/Xba1 site of the modified pGEX-2T vector. Each pair of oligos were designed such that when annealed they mimicked a digested BamHI site at the 5' end and a XbaI site at the 3' end. The 3' end of each pair of annealed oligos also included a terminal stop codon before the restriction site. The oligos used in this study are shown in Table 1 below

TABLE 1

Oligos used to generate the osteopontin fragments describecL STB10a-aa17 (5'), STB20-aa314 (3'), STB32-aa168 (3'), TbrRAD-aa168RAD (3'), STB30-aa115 (3'), STB short-aa125 (5') were used as PCR primers to the 5' and 3' ends as indicated. STB54A-aa150-169 antisense, STB54-aa150-169 sense, STB53A-aa146-160 antisense, STB53-aa146-160 sense, STB52A-aa139-153 antisense, STB52-aa139-153 sense, STB51A-aa132-146 antisense, STB51-aa132-146 sense, STB50a-aa125-139 antisense, STB50-aa125-139 sense were annealed together as appropiate and inserted into the modified pGEX vector as described.

| Oligo Name | Sequence 5'->3' |
|---|---|
| STB10a- aa17 (5') | ACTCTGGATCCATACCAGTTAAACAGGCTGATTCT (SEQ ID NO:24) |
| STB20- aa314 (3') | AGTCTCTAGATTAATTGACCTCAGAAGATGCACTATC (SEQ ID NO:25) |
| STB32- aa168 (3') | AGTCTCTAGATTACCTCAGTCCATAAACCACACTATC (SEQ ID NO:26) |
| ThrRAD-aa168RAD (3') | AGTCTCTAGATTACCTCAGTCCATAAACCAGACTATCAGCTCG (SEQ ID NO:27) |
| STB30- aa115 (3') | AGTCTCTAGATTAAATCAGTGTCATCTACATCATCAGA (SEQ ID NO:28) |
| STB long-aa115 (5') | AGTCGGATCCGATTCTCACCAGTCTGATGAG (SEQ ID NO:29) |
| STB short-aa125 (5') | AGTCGGATCCCATTCTGATGAATCTGATGA (SEQ ID NO:30) |

TABLE 1-continued

Oligos used to generate the osteopontin fragments describecL STB10a-aa17 (5'),
STB20-aa314 (3'), STB32-aa168 (3'), TbrRAD-aa168RAD (3'), STB30-aa115
(3'), STB short-aa125 (5') were used as PCR primers to the 5' and 3' ends
as indicated. STB54A-aa150-169 antisense, STB54-aa150-169 sense, STB53A-aa146-160
antisense, STB53-aa146-160 sense, STB52A-aa139-153 antisense, STB52-aa139-153 sense,
STB51A-aa132-146 antisense, STB51-aa132-146 sense, STB50a-aa125-139 antisense,
STB50-aa125-139 sense were annealed together as appropiate and inserted into the
modified pGEX vector as described.

| Oligo Name | Sequence 5'->3' |
|---|---|
| STB54A-aa150-169 antisense | CTAGATTACCTCAGTCCATAAACCACACTATCAGCTCGGCCATCATATGTGTCTACA (SEQ ID NO:31) |
| STB54-aa150-169 sense | GATCTGTAGACACATATGATGGCCGAGCTGATAGTGTGGTTTATGGACTGAGGTAA (SEQ ID NO:32) |
| STB53A-aa146-160 antisense | CTAGATTAAGCTCGGCCATCATATGTGTCTACTGTGGGGACAACTGGAGTGAAA (SEQ ID NO:33) |
| STB53-aa146-160 sense | GATCTTTCACTCCAGTTGTCCCCACAGTAGACACATATGATGGCCGAGCTTAAT (SEQ ID NO:34) |
| STB52A-aa139-153 antisense | CTAGATTATACTGTGGGGACAACTGGAGTGAAAACTTCGGTTGCTGGCAGGTCA (SEQ ID NO:35) |
| STB52-aa139-153 sense | GATCTGACCTGCCAGCAACGGAAGTTTTCACTCCAGTTGTCCCCACAGTATAAT (SEQ ID NO:36) |
| STB51A-aa132-146 antisense | CTAGATTAGAAAACTTCGGTTGCTGGCAGGTCCGTGGGAAAATCAGTGACCAGA (SEQ ID NO:37) |
| STB51-aa132-146 sense | GATCTCTGGTCACTGATTTTCCCACGGACCTGCCAGCAACCGAAGTTTTCTAAT (SEQ ID NO:38) |
| STB50A-125-139 antisense | CTAGATTAGTCCGTGGGAAAATCAGTGACCAGTTCATCAGATTCATCAGAATGA (SEQ ID NO:39) |
| STB50-aa125-139 sense | GATCTCATTCTTCTGATGAATCTGATGAACTGGTCACTGATTTTCCCACGGACTTAT (SEQ ID NO:40) |

All the GST fusion proteins of OPN were expressed using the UT5600 bacterial strain (New England Biolabs). The deficiency of the periplasmic protease in UT5600 enabled production of intact OPN, which is otherwise cleaved at lysines aa170, 172 or 174 when produced in XL-1 Blue cells. The GST-FN8-10 and GST-CS-1 fusion proteins were both expressed in the XL-1 blue strain of bacteria. After transformation with the appropriate vectors, ampicillin resistant colonies were grown overnight in 2TY media containing 100 μg/ml ampicillin at 37° C. The overnight culture were back diluted 1:40 and grown for a further 2-3 hrs at 37° C. Protein expression was induced with 0.5 mM isopropyl-1-thio-B-D-galactopyranoside (IPTG) for 2 hr at 37° C. Cells were pelleted and resuspended in lysis buffer (25 mM Hepes (pH7.5), 150 mM NaCl, 2 mM DTT with Complete Protease Inhibitors (Boehringer)), then lysed by sonication. The supernatant was prepared by centrifugation at 10 000 rpm and the GST fusion proteins adsorbed onto reduced glutathione conjugated SEPHAROSE beads (Pharmacia). Protein-bound beads were washed 4 times with 25 column volumes of 25 mM Hepes (pH7.5), 150 mM NaCl, 2 mM DTT before elution with 5 mM reduced glutathione (Sigma) in 25 mM Hepes (pH7.5), 150 mM NaCl, 2 mM DTT. Peak fractions were pooled, concentrated and then dialyzed into PBS. Protein concentrations were determined using the Coomassie Plus Protein Assay Reagent (Pierce). The integrity and purity of each preparation was analyzed both by SDS-PAGE and by mass spectrometry.

The recombinant human zz-VCAM and zz-MAdCAM, comprising the extracellular domain of each molecule coupled to the immunoglobulun binding domain of protein-A, were expressed in baculovirus and purified using an IgG coupled affinity column.

Peptides

The parent peptide SVVYGLR-COOH (SEQ ID NO: 4), scrambled peptide GRVLYSV-COOH (SEQ ID NO: 5) and the capped peptide SVVYGLR-CONH$_2$ (SEQ ID NO: 4) was synthesized in house. The synthetic peptides in which each residue of the SVVYGLR motif was individually mutated to Alanine were purchased from Cambridge Research Biochemicals Ltd.

Adhesion Assays (i) General Adhesion Assays

All proteins were coated onto MAXISORP plates (Nunc) overnight at 4° C. Each protein was diluted in PBS at the concentrations indicated, and a total volume of 100 μl added per well. Plates were washed twice in PBS then blocked with 3% BSA/PBS for 1 hr at 37° C., and finally washed twice in PBS. Routinely HL60 cells were pelleted and washed once in HBSS (Sigma) then spread in 25 mM Hepes 7.5, HBSS at $2 \times 10^6$ ml$^{-1}$ (100 μl per well) in the presence of 0.2 mM MnCl$_2$ and 50 ng/ml TPA, with other additions as indicated. J6 cells were likewise pelleted and washed once in HBSS (Sigma) then spread in 25 mM Hepes (pH7.5), HBSS at $2 \times 10^6$ ml$^{-1}$ (100 μl per well) in the presence of 0.2 mM MnCl$_2$ and other additions as indicated. For antibody inhibition cells were preincubated with the antibody (10 μg/ml) on ice for 10 minutes. Cells were then allowed to attach for 35 minutes at 37° C., washed twice in PBS, once in ethanol, and fixed in ethanol for 20 minutes at room temperature. For quantitation cells were visualised by staining with 0.1% crystal violet (Sigma) for 10 minutes then lysed in 0.5% TRITON X-100 (Sigma) and read at 570 nM in a Wallac Victor plate reader.

a problem when members of the αv integrin family are expressed as these integrins bind OPN with high affinity. The limited repertoire of integrin expression, particularly the absence of αv integrins, makes J6 and HL60 cells ideal for studying the α4β1 interaction with OPN.

TABLE 2

FACS analysis of integrin expression on HL60 and J6 cells. The repertoire of integrins expressed on HL60 and J6 was analysed as indicated. Results are expressed as the median relative to the isotype control antibody.

| Cell Type | IgG | α1 | αvβ3 | β6 | β2 | α5 | α4 | αv | α9 | αL | αm |
|---|---|---|---|---|---|---|---|---|---|---|---|
| HL60 | 1 | 31.1 | 1.4 | 3.6 | 17.8 | 19.1 | 19.8 | 3 | 0.9 | 19.6 | 1.2 |
| J6 | 1 | 36.1 | 1.4 | 0.8 | 3.2 | 11.1 | 25.2 | 1.9 | 1 | 1.9 | 0.8 |

(ii) α4β7 Adhesion Assay

The recombinant zz-MAdCAM was absorbed onto Maxisorp plate pre-coated for 2.5 hours at 37° C. with 100 µL of human IgG, and then washed twice with PBS. For capture the recombinant zz-MAdCAM was diluted to the appropriate concentration in 3% BSA/PBS, 100 µl added to each well, and incubated overnight at 4° C. Prior to use plates were washed twice in PBS.

For the α4β7 adhesion assay RPMI8866 cells were washed in cation free HBSS supplemented with 1 mM EDTA, pelleted and labeled by incubating with BCECF (Molecular Probes) in cation-free BSS at 37° C. for 10 minutes. At this stage cells were also co-incubated with 1 µl/ml human IgG to block endogenous Fc receptors. Cells were then washed once more in cation-free HESS and then used in the adhesion assay at a final concentration of $3 \times 10^6$ cells ml$^{-1}$ in the presence of the appropriate treatment as indicated. To prevent cells clumping the assay plate was finally centrifuged at 400 rpm for 3 minutes without the brake. Cells were then incubated for 20 minutes at 37° C. and then washed twice in PBS before reading directly in a plate reader. For antibody inhibition studies the cells were preincubated with the appropriate antibody at 20 µl/ml for 5 minutes at room temperature prior to being placed in the incubator.

Results

Expression of Recombinant OPN Fragments

To define the α4β1 binding site within OPN we have used GST fusion proteins of human OPN as these have previously been shown to support adhesion as efficiently as the native protein. To obtain undegraded recombinant protein all fusions were expressed in the Ion protease deficient strain, UT5600. Mass spectrometric analysis confirmed that the GST-OPN fusions were not degraded, and the proteins were greater than 95% pure as judged by SDS-PAGE (data not shown). A schematic representation of the larger fusion proteins used in this study is shown in FIG. 1.

Integrin Profiles of J6 and HL60 Cells

To analyse the interaction between α4β1 and OPN we have used two non-adherent cell lines, J6 and HL60. FACS analysis (Table 2) showed that these two cells types express a limited repertoire of integrins. Of the integrins analyzed J6 express only α5β1 and α4β, while HL60 express α4β1, α5β1 and αLβ2. Studying the interaction of integrins with OPN is often complicated by the expression of a number of integrins capable of binding OPN on one cell type. This is particularly HL60 and J6 Cells Bind Intact Osteopontin via α4β1

An interaction between α4β1 and bovine OPN was originally identified using HL60 cells, however binding required the presence of both TPA and a β1 integrin activating antibody, 8A2, to promote α4β1 into a higher activation state. To assess the interaction with human OPN J6 and HL60 cells were allowed to adhere to a GST fusion protein corresponding to intact OPN (aa17-314) in the presence of function blocking antibodies (FIG. 2). J6 cells adhered to intact OPN in the presence of Mn$^{2+}$ alone (FIG. 2A). To mimic the conditions required for HL60 binding [21], HL60 cells were allowed to adhere in the presence of both 50 ng/ml TPA and Mn$^{2+}$, the Mn$^{2+}$ substituting for the activating β1 antibody 8A2 (FIG. 2B). Adhesion of both cell types to intact OPN was inhibited by function blocking antibodies against both α4 and β1 integrins. A function blocking antibody directed against α5 integrin reduced binding to OPN, but only to the same extent as an non-specific isotype control antibody. Therefore both J6 and HL60 cells adhere to full length OPN via α4β1, with little or no contribution from another adhesion receptor.

Mapping the α4β1 Binding Site in OPN

To map the region of OPN that binds α4β1, J6-cells were adhered to GST fusion proteins corresponding to aa17-314, 17-168 and 17-115 of OPN. aa17-168 represents the fragment of OPN generated in vivo by thrombin cleavage at aa168, while aa17-115 corresponds to the N-terminus of OPN truncated past the RGD motif, which interacts with the integrins, αvβ3, αvβ5, αvβ1, α8β1 and α5β1. To ensure that binding to these fragments was mediated by α4β1 cells were also adhered in the presence of the α4β1 inhibitor BIO1211 (Lin et al, 1999). J6 cells adhered to intact (aa17-314) and thrombin cleaved (aa17-168) OPN, however making the additional truncation to aa115 (aa17-115) abrogated binding (FIG. 3). As expected adhesion to aa17-314 was completely dependent upon α4β1, being blocked by BIO1211. However adhesion to aa17-168 was not totally blocked by the α4β1 inhibitor, although α4β1 clearly bound this fragment. This additional adhesion to the thrombin cleaved fragment is mediated by α5β1, which interacts with the RGD motif upon truncation of the protein to aa168. That BIO1211 specifically blocks α4β1 mediated adhesion to CS-1 and not α5β1 mediated adhesion to Fn repeats 8-10 demonstrates that it is specific for α4β1 at the concentration used. Collectively this data localizes the α4β1 binding site to between aa115-168.

To confirm that this region (aa115-168) contains the α4β1 binding site and to narrow the region down further, J6 cells were adhered to GST fusion proteins corresponding to aa115-

168 and 125-168 of OPN, in the presence and absence of BIO1211 (FIG. 4A). J6 cells bound both fusion protein via α4β1, as adhesion was reduced by BIO1211. As both fusion proteins contain the RGD motif binding via α5β1 is evident at higher matrix concentrations in the presence of BIO1211. α4β1 can interact with a diverse range of motifs including RGD under certain conditions. To determine whether α4β1 binds the RGD motif in OPN, the RGD in the thrombin cleaved fragment (aa17-168) was mutated to RAD (aa17-168RAD). This mutation ablates adhesion via RGD dependent integrins but did not affect binding of J6 cells to aa17-168RAD via α4β1 (FIG. 4B) Introducing this RAD mutation into the thrombin cleaved fragment blocked adhesion via α5β1, as binding was completely blocked by BIO1211. The α4β1 binding site is therefore contained within aa125-168 and does not require a functional RGD motif.

To define the α4β1 binding site within aa125-168, the region was analyzed in detail by expressing a series of overlapping GST fusion proteins (FIG. 5A). To eliminate cell binding through the cryptic α4β1 site, the Gly of the RGD site was mutated to Ala in peptides 146-160 and 153-168. Surprisingly two fusion protein corresponding to aa132-146 and aa153-168 supported J6 cell adhesion (FIG. 5B), which was mediated by α4β1 as BIO1211 blocked adhesion to both peptides (FIG. 5C). The first sequence aa132-146 is non conserved, present only in human, bovine and possibly pig OPN, while the second sequence aa153-168 is conserved across all species (FIG. 6). This data is consistent with there being two α4β1 binding sites within the N-terminus of OPN capable of supporting J6 cell adhesion via α4β1.

The minimal sequences for the two sites are likely to be FPTDLPA (SEQ ID NO: 6) (aa136-142) and RGDSVVYGLR (SEQ ID NO: 41) (aa159-168). The peptide FPTDLPA (SEQ ID NO: 6) (aa136-142) lies within a non-conserved region, and would only be predicted to act as an α4β1 binding site in human, bovine and possibly pig OPN. However the second motif RGDSVVYGLR (SEQ ID NO: 41) (aa159-168) is conserved across all species (FIG. 6). Although the data presented shows binding of J6 cells, experiments performed with HL60 cells were identical.

A Synthetic Peptide SVVYGLR (SEQ ID NO: 4) but Not FPTDLPA (SEQ ID NO: 6) Blocks Binding to CS-1 by α4β1

Figure 7:
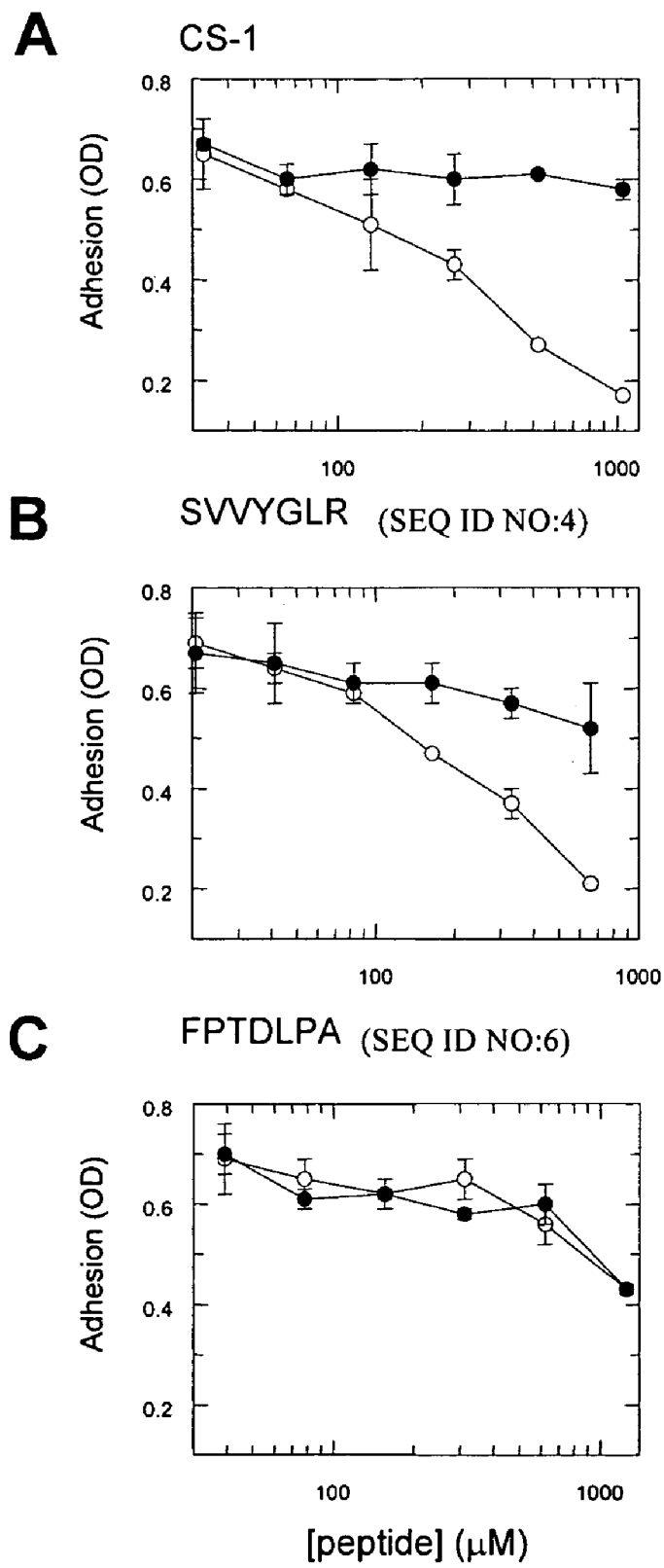
FIG. 7 shows the degree of inhibition of the α4β1-CS-1 interaction by various OPN derived peptides. J6 cells were allowed to attach to wells coated with GST-CS-1 in the presence of CS-1 peptide (open circles) and scrambled control peptide (closed circles) shown in (A); SVVYGLR (SEQ ID NO: 4) (open circles) and the scrambled control peptide, GRVLYSV (SEQ ID NO: 5) (closed circles) shown in (B); FPTDLPA (SEQ ID NO: 6) (open circles) and the scrambled control peptide, PDFPLAT (SEQ ID NO: 7) (closed circles) shown in (C). Cells were incubated at 37° C. for 35 minutes. This data is representative of at least four similar experiments and each data point represents the mean±SD of duplicate points.

The overlapping fusion proteins used to analyse α4β1 binding within the region aa125-168 suggest that the critical motifs in each fusion protein are FPTDLPA (SEQ ID NO: 6) (within aa132-146) and RGDSVVYGLR (SEQ ID NO: 41) (within aa153-168). The site within aa153-168 can be narrowed further to SVVYGLR (SEQ ID NO: 4), as the RGD motif is not critical for binding. To determine whether the potential binding sites could act as competitive inhibitors of α4β1, two peptides, SVVYGLR (SEQ ID NO: 4) and FPTDLPA (SEQ ID NO: 6), were synthesized and the ability of each to inhibit binding to a GST fusion protein corresponding to the CS-1 fragment of fibronectin was assessed (FIG. 7).

SVVYGLR (SEQ ID NO: 4), but not its scrambled control peptide blocked adhesion to CS-1 (FIG. 7B). This peptide was only slightly less potent at blocking adhesion to CS-1 than the CS-1 peptide itself (FIG. 7A), indicating that SVVYGLR (SEQ ID NO: 4) is an effective inhibitor of α4β1 binding. Conversely the peptide FPTDLPA (SEQ ID NO: 6) was unable to inhibit binding to CS-1 compared to the scrambled control at the concentration of CS-1 ligand (FIG. 7C). It did however show weak inhibition of binding over the scrambled control peptide at lower matrix concentrations (data not shown), consistent with this peptide making a low affinity interaction with the integrin. This suggests that of the two peptides identified, SVVYGLR (SEQ ID NO: 4) is the major α4β1 binding site within OPN, while FPTDLPA (SEQ ID NO: 6) represents a second, lower affinity binding site.

The Osteopontin SVVYGLR (SEQ ID NO: 4) Motif Supports Adhesion via α4β1 and α4β7

α4β1 and α4β7 are related integrins which recognize common sites in certain ligands such as VCAM-1 and CS-1. These integrins, along with α9β1, form a sub-family of receptors defined by both their sequence homology and overlapping ligand binding repertoire. To analyse the interaction of α4β7 with the SVVYGLR (SEQ ID NO: 4) motif RPMI8866 cells which express α4β7, and small amounts of α4β1 and α5β1 were used. Importantly these cells do not express any detectable αv integrin one of the major alternate sub-family of integrins known to interact with osteopontin.

Figure 8:
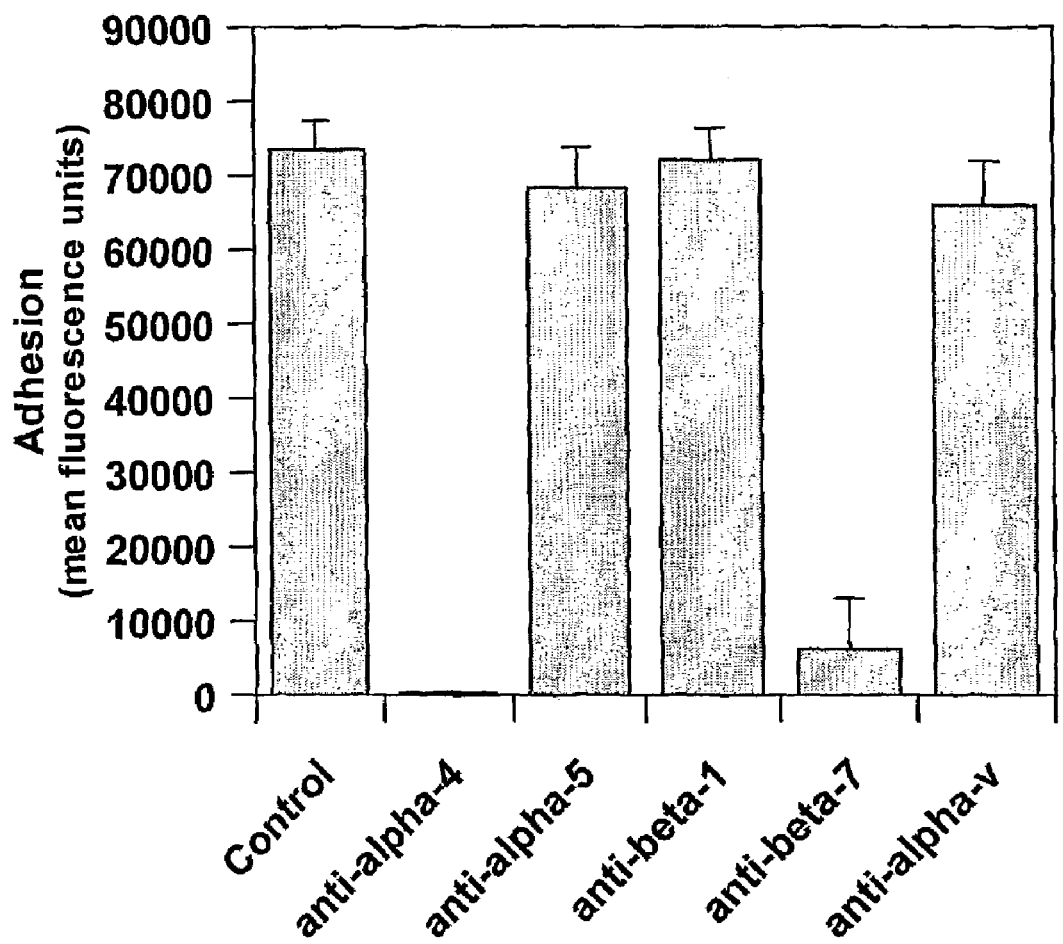
FIG. 8 shows that α4β7 binds the SVVYGLR (SEQ ID NO: 4) motif of osteopontin. RPMI8866 cells were allowed to adhere to a GST fusion protein incorporating amino acid residues 153-168 of osteopontin SVVYGLR (SEQ ID NO: 4) peptide in the presence or absence of anti-functional integrin antibodies (20 μg/ml), as indicated. Cells were incubated at 37° C. for 20 minutes. This data is representative of at least four similar experiments and each data point represents the mean±SD of duplicate points.

To demonstrate that α4β7 binds the SVVYGLR (SEQ ID NO: 4) motif RPMI8866 cells were allowed to adhere to the GST fusion protein corresponding to amino acid residues 153-168 of osteopontin in the presence and absence of function-blocking anti-integrin antibodies (FIG. 8). In the intact protein this sequence also contains the RGD motif of osteopontin, which binds αv integrins and α5β1, therefore to prevent interactions via the RGD motif the Gly was mutated to Ala. Adhesion of RPMI8866 cells to amino acid residues 153-168 was blocked by α4 and β7 function blocking antibodies, but not by antibodies against β1, αv or α5 integrin. This demonstrates that RPMI8866 cells bind the SVVYGLR (SEQ ID NO: 4) motif of osteopontin via α4β7. Although these cells express a small amount of α41 this receptor is not making a significant contribution to binding as the β1 anti-functional antibody had no effect.

A Synthetic Peptide SVVYGLR (SEQ ID NO: 4) Inhibits α4β7 Binding to MAdCAM

Figure 9:
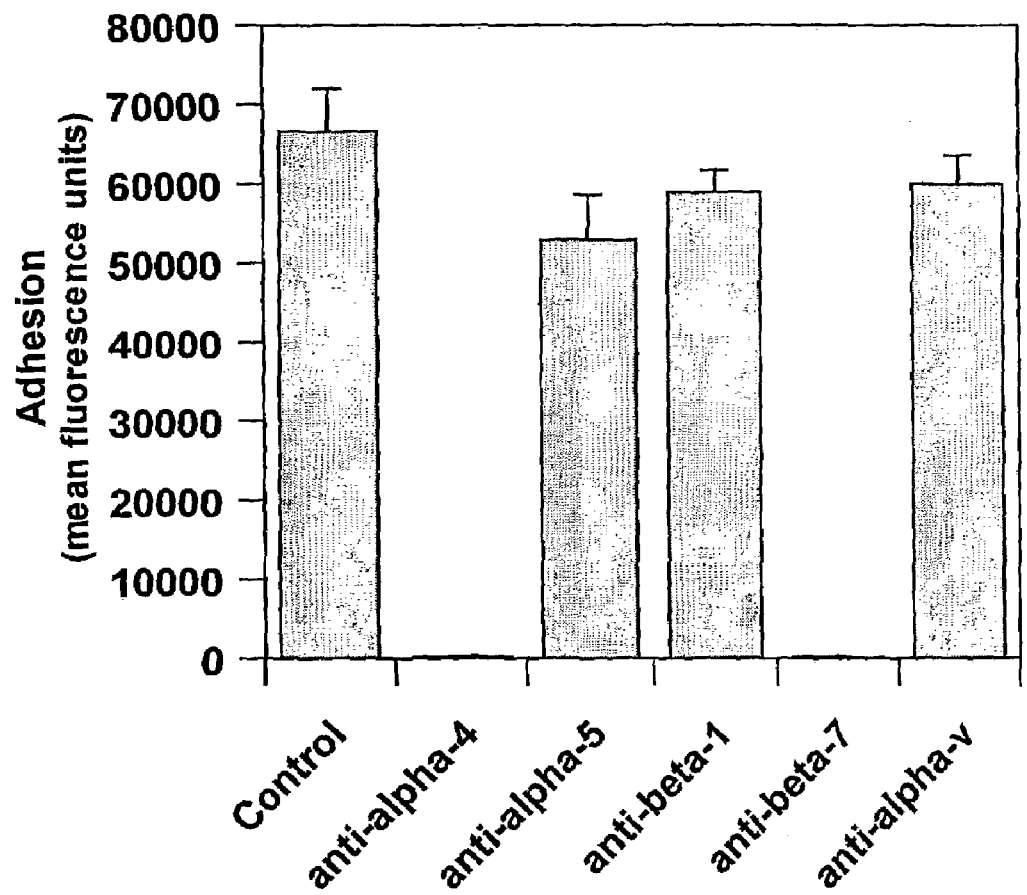
FIG. 9 shows that RPMI8866 cells bind zz-MAdCAM via α4β7. RPMI8866 cells were allowed to adhere to zz-MAdCAM in the presence or absence of anti-functional integrin antibodies (20 μg/ml), as indicated. Cells were incubated at 37° C. for 20 minutes. This data is representative of at least four similar experiments and each data point represents the mean±SD of duplicate points.
Figure 10:
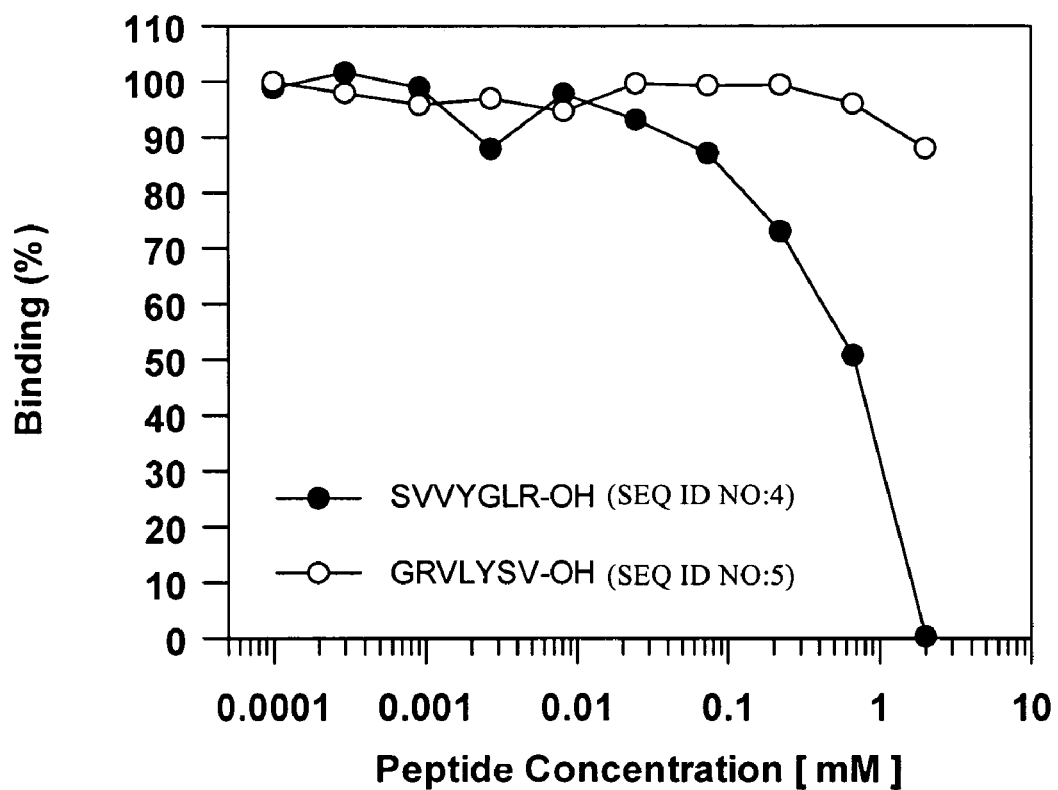
FIG. 10 shows that peptide SVVYGLR (SEQ ID NO: 4) inhibits α47 binding to MAdCAM. RPMI8866 cells were adhered to zz-MAdCAM in the presence of varying concentrations of parent SVVYGLR (SEQ ID NO: 4) or scrambled GRVLYSV (SEQ ID NO: 5) peptides. This data is representative of at least three experiments, and each data point represents the mean±SD of duplicate points.

The peptide SVVYGLR (SEQ ID NO: 4) inhibits α4β1 binding to a GST fusion protein corresponding to the CS-1 alternatively spliced fragment of fibronectin (FIG. 7). To confirm that this peptide could also act as an α4β7 antagonist its ability to inhibit RPMI8866 cell adhesion to MAdCAM was assessed. RPMI8866 cells bind MAdCAM exclusively through α4β7, as blocking antibodies against the α4 integrin subunit and the β7 integrin subunit but not the β1 integrin subunit blocked adhesion to zz-MAdCAM (FIG. 9). The SVVYGLR (SEQ ID NO: 4) peptide inhibited adhesion of the RPMI8866 cells to MAdCAM, while the scrambled control peptide had no effect (FIG. 10). This data demonstrates that the SVVYGLR (SEQ ID NO: 4) motif derived from OPN also acts as an antagonist of α4β7 as it blocks binding to MAdCAM.

Analysis of Structural Elements of the SVVYGLR (SEQ ID NO: 4) Motif Critical for Inhibition of α4 Integrins As the SVVYGLR (SEQ ID NO: 4) peptide effectively blocks adhesion of α4β1 to CS-1 and α4β7 to MAdCAM this approach was used to determine the structural elements of the SVVYGLR (SEQ ID NO: 4) motif that interact with α4β1 and α4β7. A number of the motifs known to interact with α4 integrins contain a critical acidic residue normally an Asp. One significant feature of the SVVYGLR (SEQ ID NO: 4) motif is that it lacks an obvious acidic group, therefore understanding how this motif binds α4 integrins could have important implications for the design of small molecule antagonists.

Figure 11:
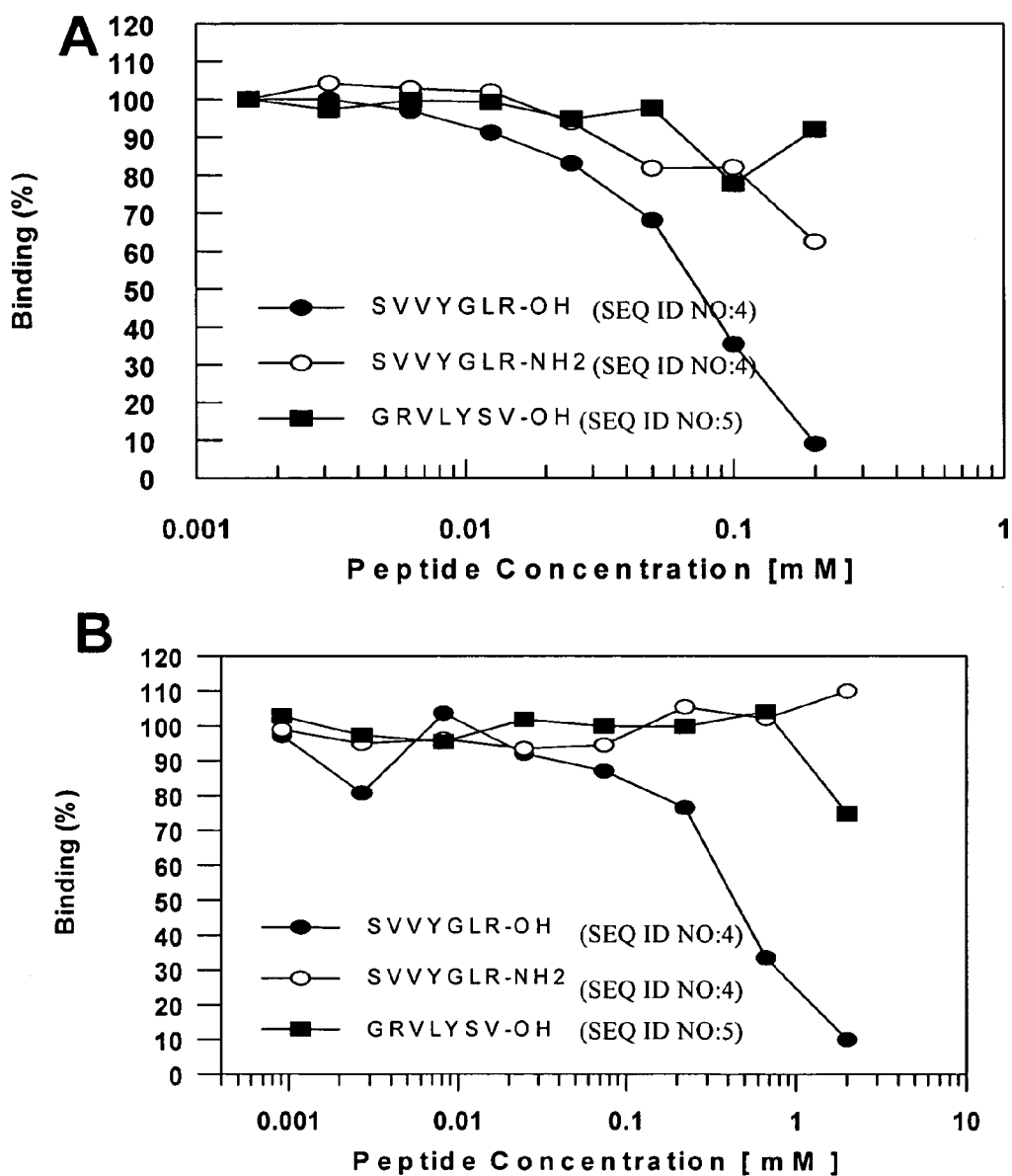
FIG. 11 shows that the acidic carboxy terminal COOH group (Arg 168) of the SVVYGLR (SEQ ID NO: 4) motif is required for inhibition of α4β1 and α4β7. (A) J6 cells were adhered to GST-CS-1 in the presence of varying concentrations of parent SVVYGLR-COOH (SEQ ID NO: 4), capped SVVYGLR-CONH2 (SEQ ID NO: 4) or scrambled GRVLYSV-COOH (SEQ ID NO: 5) peptides. This data is representative of at least three experiments. (B) RPMI8866 cells were adhered to zz-MAdCAM in the presence of varying concentrations of parent SVVYGLR(SEQ ID NO: 4), capped SVVYGLR (SEQ ID NO: 4)-CONH2 or scrambled GRVLYSV (SEQ ID NO: 5) peptides. This data is representative of at least three experiments, and each data point represents the mean±SD of duplicate points.

The SVVYGLR (SEQ ID NO: 4) site is located immediately N-terminal to the thrombin cleavage site, which occurs at Arg168. It is possible that thrombin cleavage at amino acid 168 reveals a free C-terminal acidic group (carboxylic acid)

enabling the SVVYGLR (SEQ ID NO: 4) motif to engage α4 integrins. To test this hypothesis a capped peptide SVVYGLR (SEQ ID NO: 4)-CONH2 was synthesized and tested for the ability to inhibit J6 and RPMI8866 cell adhesion FIGS. 11A and B). Removing the acidic carboxy terminus abrogated the ability of this peptide to inhibit adhesion via both α4β1 and α4β7.

This data indicates that the free acidic carboxy terminus of the SVVYGLR (SEQ ID NO: 4) motif is providing an acidic group which is essential for its interaction with α4 integrins. Moreover this data confirms that thrombin cleavage of osteopontin at amino acid residue 168 is required for α4β1 and α4β7 ligation.

Figure 12:
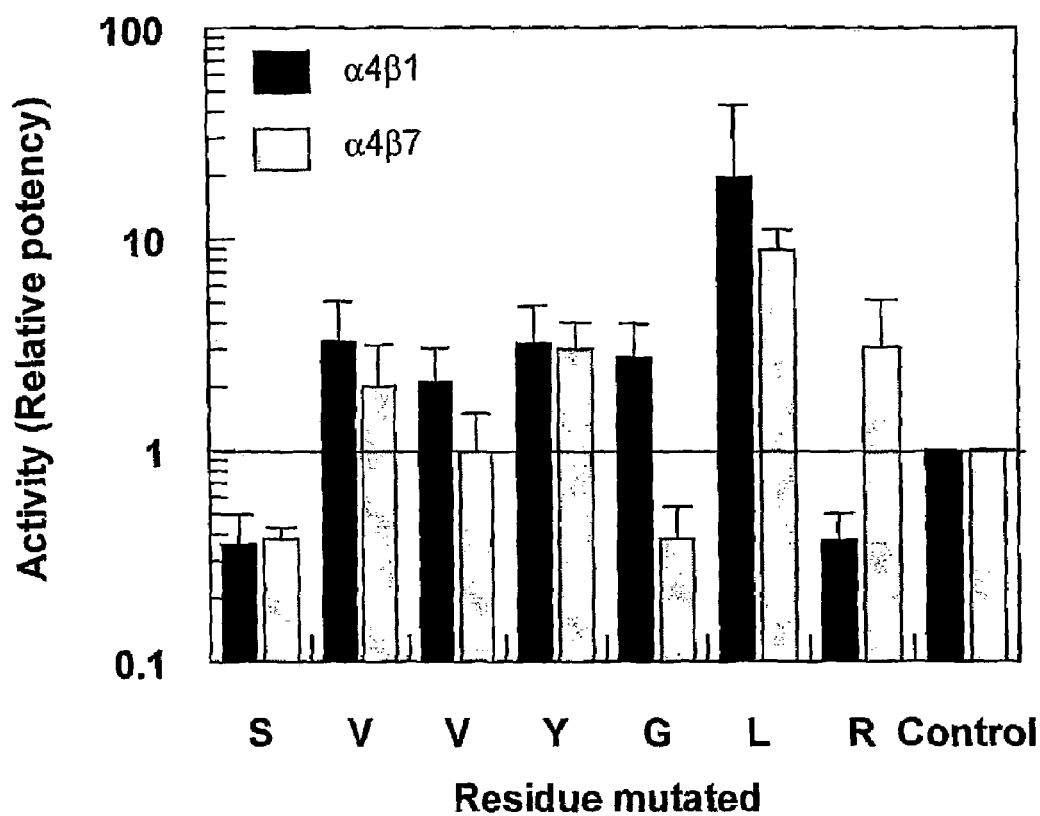
FIG. 12 shows the identification of key residues within SVVYGLR (SEQ ID NO: 4) required for inhibition of α4β1 and α4β7 binding. J6 and RPMI8866 cells were allowed to adhere to CS-1 and zz-MAdCAM in the presence of a series of SVVYGLR (SEQ ID NO: 4) peptides in which each residue was individually mutated to alanine. Each residue mutated to alanine is indicated. The data are expressed as a relative potency (RP) compared to the parent peptide SVVYGLR (SEQ ID NO: 4), and represent to mean of 4 experiments.

To further determine which other elements of the SVVYGLR (SEQ ID NO: 4) motif are required for the interaction with α4 integrins, a series of synthetic peptides were generated in which each amino acid was individually mutated to alanine. The ability of each peptide to block adhesion of J6 and RPMI8866 cells to GST-CS-1 and zz-MAdCAM respectively was then assayed. The ability of each peptide to inhibit binding is shown in FIG. 12 expressed as a relative potency compared to the activity of the parent peptide SVVYGLR-COOH (SEQ ID NO: 4). This analysis clearly shows that Leu167 is also crucial. Mutating this residue results in a relative potency similar to that observed with the blocked peptide SVVYGLR-CONH2 (SEQ ID NO: 4) or the scrambled control (data not shown).

Figure 13:
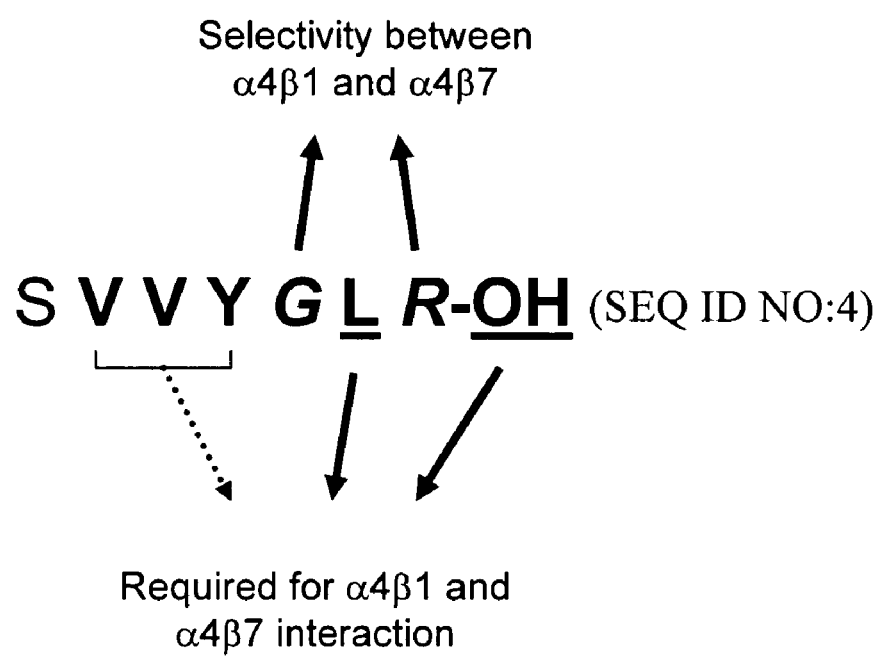
FIG. 13 shows a summary of the key elements of the SVVYGLR (SEQ ID NO: 4) motif. Leu167 and the free carboxy terminal —COOH group of Arg168 are required for the interaction with α4β1 and α4β7. Val163, Val164 and Tyr165 make a minor contribution to binding. Mutating Arg168 and Gly166 introduces a degree of selectivity between α4β1 and α4β7.

A number of other residues were also found to make a minor contribution to the pharmacophore in particular Val163 and Tyr165, as mutation of these reduced the potency against both integrins. The observation that Tyr165 makes only a minor contribution to the α4 pharmacophore is interesting as this residue appears to be critical for the interaction with α9β1. Surprisingly mutation of Arg168 has opposite effects on the potency of the peptide against α4β1 and α4β7. Mutating this residue to Ala results in a peptide that is more potent against α4β1 but less potent against α4β7. Therefore the constituent at this position may confer some selectivity between α4β1 and α4β7. Collectively this data shows that Leu167 and the free carboxy terminus of Arg168 are the most critical residues within the SVVYGLR (SEQ ID NO: 4) motif for binding to α4 integrins. This data is summarised in FIG. 13.

The invention claimed is:

1. A method for identifying a product which is capable of disrupting an interaction between amino acids 162 to 168 of human osteopontin (OPN) and an α4 integrin, which method comprises:
   (i) providing, as a first component, a polypeptide which comprises the amino acid sequence selected from the group consisting of: SVVYGLR (SEQ ID NO: 4) and RADSVVYGLR (SEQ ID NO: 19);
   (ii) providing, as a second component, an α4 integrin;
   (iii) contacting the two components under conditions that would permit the two components to interact and determining the degree of interaction between the two components
   (iv) contacting the two components with a test product under conditions that would permit the two components to interact in the absence of the test product and determining the degree of interaction between the two components; and
   (v) determining whether the test product is capable of disrupting the interaction between the first and second components by comparing the degrees of interaction found in (iii) and (iv).

2. A method according to claim 1, wherein the α4 integrin used as a second component is α4β1.

3. A method for identifying a product which is capable of binding to amino acids 162 to 168 of human OPN, which method comprises:
   (i) providing a first component that is a polypeptide which comprises of the amino acid sequence selected from the group consisting of: SVVYGLR (SEQ ID NO: 4) and RADSVVYGLR (SEQ ID NO: 19);
   (ii) contacting the first component with an α4 integrin under conditions that, in the absence of a test product, would lead to an interaction between the first component and the α4 integrin;
   (iii) contacting the first component with an α4 integrin and a test product under the same conditions that lead to an interaction between the first component and the α4 integrin in (ii); and
   (iv) determining whether the test product is capable of binding to the first component.

4. A test kit suitable for use in identifying a product which is capable of disrupting an interaction between amino acids 162 to 168 of human OPN and an α4integrin, which kit comprises:
   (i) a first component that is a polypeptide which comprises the amino acid sequence selected from the group consisting of: SVVYGLR (SEQ ID NO: 4) and RADSVVYGLR (SEQ ID NO: 19); and
   (ii) an α4 integrin.

5. A test kit according to claim 4, wherein the α4 integrin is α4β1.

6. A polypeptide comprising the amino acid sequence RADSVVYGLR (SEQ ID NO: 19).

7. A pharmaceutical composition comprising a pharmaceutically acceptable carrier or diluent and, as active ingredient, a polypeptide comprising the amino acid sequence RADSVVYGLR (SEQ ID NO: 19).

8. A method for identifying a product which is capable of disrupting an interaction between amino acids 162 to 168 of human osteopontin (OPN) and an α4integrin, which method comprises:
   (i) providing, as a first component, a polypeptide which consists of the amino acid sequence selected from the group consisting of: SVVYGLR (SEQ ID NO: 4), RGDSVVYGLR (SEQ ID NO: 41) and RADSVVYGLR (SEO ID NO: 19);
   (ii) providing, as a second component, an α4 integrin;
   (iii) contacting the two components under conditions that would permit the two components to interact and determining the degree of interaction between the two components
   (iv) contacting the two components with a test product under conditions that would permit the two components to interact in the absence of the test product and determining the degree of interaction between the two components; and
   (v) determining whether the test product is capable of disrupting the interaction between the first and second components by comparing the degrees of interaction found in (iii) and (iv).

9. A method according to claim 8, wherein the α4 integrin used as a second component is α4β1.

10. A method for identifying a product which is capable of binding to amino acids 162 to 168 of human OPN, which method comprises:
    (i) providing a first component that is a polypeptide which consists of the amino acid sequence selected from the group consisting of: SVVYGLR (SEQ ID NO: 4), RGDSVVYGLR (SEQ ID NO: 41) and RADSVVYGLR (SEQ ID NO: 19);
    (ii) contacting the first component with an α4 integrin under conditions that, in the absence of a test product, would lead to an interaction between the first component and the α4 integrin;
    (iii) contacting the first component with an α4 integrin and a test product under the same conditions that lead to an interaction between the first component and the α4 integrin in (ii); and
    (iv) determining whether the test product is capable of binding to the first component.

11. A test kit suitable for use in identifying a product which is capable of disrupting an interaction between amino acids 162 to 168 of human OPN and an α4integrin, which kit comprises:
  (i) a first component that is a polypeptide which consists of the amino acid sequence selected from the group consisting of: SVVYGLR (SEQ ID NO: 4), RGDSVVYGLR (SEQ ID NO: 41) and RADSVVYGLR (SEQ ID NO: 19); and
  (ii) an α4 integrin.

12. A test kit according to claim 11, wherein the α4 integrin is α4β1.

13. A polypeptide consisting of the amino acid sequence selected from the group consisting of: RGDSVVYGLR (SEQ ID NO: 41) and RADSVVYGLR (SEQ ID NO: 19).

14. A pharmaceutical composition comprising a pharmaceutically acceptable carrier or diluent and, as active ingredient, a polypeptide consisting of the amino acid sequence selected from the group consisting of: RGDSVVYGLR (SEQ ID NO: 41) and RADSVVYGLR (SEO ID NO: 19).

* * * * *

SEQUENCE LISTING

```
<160> NUMBER OF SEQ ID NOS: 56

<210> SEQ ID NO 1
<211> LENGTH: 314
<212> TYPE: PRT
<213> ORGANISM: Homo sapiens

<400> SEQUENCE: 1

Met Arg Ile Ala Val Ile Cys Phe Cys Leu Leu Gly Ile Thr Cys Ala
 1               5                  10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205
```

```
Gln Asp Leu Asn Ala Pro Ser Asp Trp Asp Ser Arg Gly Lys Asp Ser
    210                 215                 220
Tyr Glu Thr Ser Gln Leu Asp Asp Gln Ser Ala Glu Thr His Ser His
225                 230                 235                 240
Lys Gln Ser Arg Leu Tyr Lys Arg Lys Ala Asn Asp Glu Ser Asn Glu
                245                 250                 255
His Ser Asp Val Ile Asp Ser Gln Glu Leu Ser Lys Val Ser Arg Glu
            260                 265                 270
Phe His Ser His Glu Phe His Ser His Glu Asp Met Leu Val Val Asp
        275                 280                 285
Pro Lys Ser Lys Glu Glu Asp Lys His Leu Lys Phe Arg Ile Ser His
    290                 295                 300
Glu Leu Asp Ser Ala Ser Ser Glu Val Asn
305                 310
```

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: When Xaa at position 2 is an amino acid, Xaa at
      position 1
      is either absent or any amino acid
<220> FEATURE:
<221> NAME/KEY: VARIANT
<222> LOCATION: (2)
<223> OTHER INFORMATION: Xaa is either absent or any amino acid
<220> FEATURE:
<221> NAME/KEY: VARIANT
<222> LOCATION: (10)
<223> OTHER INFORMATION: Xaa is absent or any amino acid
<220> FEATURE:
<221> NAME/KEY: VARIANT
<222> LOCATION: (11)
<223> OTHER INFORMATION: When Xaa at position 10 is an amino acid, Xaa at
      position 11
      is absent or any amino acid

<400> SEQUENCE: 2

```
Xaa Xaa Phe Pro Thr Asp Leu Pro Ala Xaa Xaa
 1               5                  10
```

<210> SEQ ID NO 3
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (1)
<223> OTHER INFORMATION: When Xaa at positions 2 and 3 are amino acids,
      Xaa at position 1
      is absent or any amino acid
<220> FEATURE:
<221> NAME/KEY: VARIANT
<222> LOCATION: (2)
<223> OTHER INFORMATION: If the Xaa at position 3 is an amino acid, Xaa
      at position 2 is absent or any amino acid
<220> FEATURE:
<221> NAME/KEY: VARIANT
<222> LOCATION: (3)
<223> OTHER INFORMATION: Xaa is absent or any amino acid

<400> SEQUENCE: 3

```
Xaa Xaa Xaa Ser Val Val Tyr Gly Leu Arg
 1               5                  10

<210> SEQ ID NO 4
<211> LENGTH: 7
<212> TYPE: PRT
<213> ORGANISM: Homo sapiens

<400> SEQUENCE: 4

Ser Val Val Tyr Gly Leu Arg
 1               5

<210> SEQ ID NO 5
<211> LENGTH: 7
<212> TYPE: PRT
<213> ORGANISM: Homo sapiens

<400> SEQUENCE: 5

Gly Arg Val Leu Tyr Ser Val
 1               5

<210> SEQ ID NO 6
<211> LENGTH: 7
<212> TYPE: PRT
<213> ORGANISM: Homo sapiens

<400> SEQUENCE: 6

Phe Pro Thr Asp Leu Pro Ala
 1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Pro Asp Phe Pro Leu Ala Thr
 1               5

<210> SEQ ID NO 8
<211> LENGTH: 8
<212> TYPE: PRT
<213> ORGANISM: Artificial Sequence
<220> FEATURE:
<223> OTHER INFORMATION: Peptide

<400> SEQUENCE: 8

Asp Phe Pro Thr Asp Leu Pro Ala
 1               5

<210> SEQ ID NO 9
<211> LENGTH: 9
<212> TYPE: PRT
<213> ORGANISM: Artificial Sequence
<220> FEATURE:
<223> OTHER INFORMATION: Peptide

<400> SEQUENCE: 9

Thr Asp Phe Pro Thr Asp Leu Pro Ala
 1               5

<210> SEQ ID NO 10
<211> LENGTH: 8
```

```
<212> TYPE: PRT
<213> ORGANISM: Artificial Sequence
<220> FEATURE:
<223> OTHER INFORMATION: Peptide

<400> SEQUENCE: 10

Phe Pro Thr Asp Leu Pro Ala Thr
 1               5

<210> SEQ ID NO 11

<400> SEQUENCE: 11

000

<210> SEQ ID NO 12
<211> LENGTH: 9
<212> TYPE: PRT
<213> ORGANISM: Artificial Sequence
<220> FEATURE:
<223> OTHER INFORMATION: Peptide

<400> SEQUENCE: 12

Asp Phe Pro Thr Asp Leu Pro Ala Thr
 1               5

<210> SEQ ID NO 13
<211> LENGTH: 10
<212> TYPE: PRT
<213> ORGANISM: Artificial Sequence
<220> FEATURE:
<223> OTHER INFORMATION: Peptide

<400> SEQUENCE: 13

Asp Phe Pro Thr Asp Leu Pro Ala Thr Glu
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Peptide

<400> SEQUENCE: 14

Thr Asp Phe Pro Thr Asp Leu Pro Ala Thr
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Peptide

<400> SEQUENCE: 15

Thr Asp Phe Pro Thr Asp Leu Pro Ala Thr Glu
 1               5                  10

<210> SEQ ID NO 16
<211> LENGTH: 8
<212> TYPE: PRT
<213> ORGANISM: Artificial Sequence
<220> FEATURE:
<223> OTHER INFORMATION: Peptide

<400> SEQUENCE: 16
```

```
Asp Ser Val Val Tyr Gly Leu Arg
 1               5

<210> SEQ ID NO 17
<211> LENGTH: 9
<212> TYPE: PRT
<213> ORGANISM: Artificial Sequence
<220> FEATURE:
<223> OTHER INFORMATION: Peptide

<400> SEQUENCE: 17

Gly Asp Ser Val Val Tyr Gly Leu Arg
 1               5

<210> SEQ ID NO 18
<211> LENGTH: 9
<212> TYPE: PRT
<213> ORGANISM: Artificial Sequence
<220> FEATURE:
<223> OTHER INFORMATION: Peptide

<400> SEQUENCE: 18

Phe Pro Thr Asp Leu Pro Ala Thr Glu
 1               5

<210> SEQ ID NO 19
<211> LENGTH: 11
<212> TYPE: PRT
<213> ORGANISM: Artificial Sequence
<220> FEATURE:
<223> OTHER INFORMATION: Peptide

<400> SEQUENCE: 19

Arg Ala Asp Ser Val Val Tyr Gly Leu Arg Pro
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (1)
<223> OTHER INFORMATION: When Xaa at position 2 is an amino acid, Xaa at
      position 1 is absent
      or any amino acid
<220> FEATURE:
<221> NAME/KEY: VARIANT
<222> LOCATION: (2)
<223> OTHER INFORMATION: Xaa is absent or any amino acid
<220> FEATURE:
<221> NAME/KEY: VARIANT
<222> LOCATION: (10)
<223> OTHER INFORMATION: Xaa is absent or any amino acid
<220> FEATURE:
<221> NAME/KEY: VARIANT
<222> LOCATION: (11)
<223> OTHER INFORMATION: When Xaa at position 10 is an amino acid, Xaa
      at position 11 is absent
      or any amino acid

<400> SEQUENCE: 20

Xaa Xaa Phe Pro Thr Asp Ile Pro Thr Xaa Xaa
 1               5                  10

<210> SEQ ID NO 21
<211> LENGTH: 11
<212> TYPE: PRT
```

```
<213> ORGANISM: Artificial Sequence
<220> FEATURE:
<223> OTHER INFORMATION: Peptide
<220> FEATURE:
<221> NAME/KEY: VARIANT
<222> LOCATION: (1)
<223> OTHER INFORMATION: When Xaa at position 2 is an amino acid, Xaa at
      position 1 is absent
      or any amino acid
<220> FEATURE:
<221> NAME/KEY: VARIANT
<222> LOCATION: (2)
<223> OTHER INFORMATION: Xaa is absent or any amino acid
<220> FEATURE:
<221> NAME/KEY: VARIANT
<222> LOCATION: (7)
<223> OTHER INFORMATION: Xaa at position 7 is Leucine or Isoleucine
<220> FEATURE:
<221> NAME/KEY: VARIANT
<222> LOCATION: (9)
<223> OTHER INFORMATION: Xaa at position 9 is Alanine or Threonine
<220> FEATURE:
<221> NAME/KEY: VARIANT
<222> LOCATION: (10)
<223> OTHER INFORMATION: Xaa is absent or any amino acid
<220> FEATURE:
<221> NAME/KEY: VARIANT
<222> LOCATION: (11)
<223> OTHER INFORMATION: When Xaa at position 10 is an amino acid, Xaa
      at position 11 is absent
      or any amino acid

<400> SEQUENCE: 21

Xaa Xaa Phe Pro Thr Asp Xaa Pro Xaa Xaa Xaa
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (1)
<223> OTHER INFORMATION: When Xaa at positions 2 and 3 are amino acids,
      Xaa at position 1 is
      absent or any amino acid
<220> FEATURE:
<221> NAME/KEY: VARIANT
<222> LOCATION: (2)
<223> OTHER INFORMATION: When Xaa at position 3 is an amino acid, Xaa at
      position 2 is absent
      or any amino acid
<220> FEATURE:
<221> NAME/KEY: VARIANT
<222> LOCATION: (3)
<223> OTHER INFORMATION: Xaa is absent or any amino acid

<400> SEQUENCE: 22

Xaa Xaa Xaa Ser Val Ala Tyr Gly Leu Lys
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (1)
<223> OTHER INFORMATION: When Xaa at positions 2 and 3 are amino acids,
      Xaa at position 1 is
      absent or any amino acid
```

```
<220> FEATURE:
<221> NAME/KEY: VARIANT
<222> LOCATION: (2)
<223> OTHER INFORMATION: When Xaa at position 3 is an amino acid, Xaa at
      position 2 is absent
      or any amino acid
<220> FEATURE:
<221> NAME/KEY: VARIANT
<222> LOCATION: (3)
<223> OTHER INFORMATION: Xaa is absent or any amino acid
<220> FEATURE:
<221> NAME/KEY: VARIANT
<222> LOCATION: (6)
<223> OTHER INFORMATION: Xaa is Valine or Alanine
<220> FEATURE:
<221> NAME/KEY: VARIANT
<222> LOCATION: (10)
<223> OTHER INFORMATION: Xaa is Arginine or Lysine

<400> SEQUENCE: 23

Xaa Xaa Xaa Ser Val Xaa Tyr Gly Leu Xaa
  1               5                  10

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
actctggatc cataccagtt aaacaggctg attct                                35

<210> SEQ ID NO 25
<211> LENGTH: 37
<212> TYPE: DNA
<213> ORGANISM: Artificial Sequence
<220> FEATURE:
<223> OTHER INFORMATION: Primer

<400> SEQUENCE: 25
agtctctaga ttaattgacc tcagaagatg cactatc                              37

<210> SEQ ID NO 26
<211> LENGTH: 37
<212> TYPE: DNA
<213> ORGANISM: Artificial Sequence
<220> FEATURE:
<223> OTHER INFORMATION: Primer

<400> SEQUENCE: 26
agtctctaga ttacctcagt ccataaacca cactatc                              37

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27
agtctctaga ttacctcagt ccataaacca cactatcagc tcg                       43

<210> SEQ ID NO 28
<211> LENGTH: 38
<212> TYPE: DNA
<213> ORGANISM: Artificial Sequence
<220> FEATURE:
<223> OTHER INFORMATION: Primer
```

<400> SEQUENCE: 28
agtctctaga ttaaatcagt gtcatctaca tcatcaga					38

<210> SEQ ID NO 29
<211> LENGTH: 31
<212> TYPE: DNA
<213> ORGANISM: Artificial Sequence
<220> FEATURE:
<223> OTHER INFORMATION: Primer

<400> SEQUENCE: 29
agtcggatcc gattctcacc agtctgatga g					31

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
agtcggatcc cattctgatg aatctgatga					30

<210> SEQ ID NO 31
<211> LENGTH: 57
<212> TYPE: DNA
<213> ORGANISM: Artificial Sequence
<220> FEATURE:
<223> OTHER INFORMATION: Primer

<400> SEQUENCE: 31
ctagattacc tcagtccata aaccacacta tcagctcggc catcatatgt gtctaca					57

<210> SEQ ID NO 32
<211> LENGTH: 57
<212> TYPE: DNA
<213> ORGANISM: Artificial Sequence
<220> FEATURE:
<223> OTHER INFORMATION: Primer

<400> SEQUENCE: 32
gatctgtaga cacatatgat ggccgagctg atagtgtggt ttatggactg aggtaat					57

<210> SEQ ID NO 33
<211> LENGTH: 54
<212> TYPE: DNA
<213> ORGANISM: Artificial Sequence
<220> FEATURE:
<223> OTHER INFORMATION: Primer

<400> SEQUENCE: 33
ctagattaag ctcggccatc atatgtgtct actgtgggga caactggagt gaaa					54

<210> SEQ ID NO 34
<211> LENGTH: 54
<212> TYPE: DNA
<213> ORGANISM: Artificial Sequence
<220> FEATURE:
<223> OTHER INFORMATION: Primer

<400> SEQUENCE: 34
gatctttcac tccagttgtc cccacagtag acacatatga tggccgagct taat					54

<210> SEQ ID NO 35

<211> LENGTH: 54
<212> TYPE: DNA
<213> ORGANISM: Artificial Sequence
<220> FEATURE:
<223> OTHER INFORMATION: Primer

<400> SEQUENCE: 35
ctagattata ctgtggggac aactggagtg aaaacttcgg ttgctggcag gtca        54

<210> SEQ ID NO 36
<211> LENGTH: 54
<212> TYPE: DNA
<213> ORGANISM: Artificial Sequence
<220> FEATURE:
<223> OTHER INFORMATION: Primer

<400> SEQUENCE: 36
gatctgacct gccagcaacc gaagttttca ctccagttgt ccccacagta taat        54

<210> SEQ ID NO 37
<211> LENGTH: 54
<212> TYPE: DNA
<213> ORGANISM: Artificial Sequence
<220> FEATURE:
<223> OTHER INFORMATION: Primer

<400> SEQUENCE: 37
ctagattaga aaacttcggt tgctggcagg tccgtgggaa atcagtgac caga        54

<210> SEQ ID NO 38
<211> LENGTH: 54
<212> TYPE: DNA
<213> ORGANISM: Artificial Sequence
<220> FEATURE:
<223> OTHER INFORMATION: Primer

<400> SEQUENCE: 38
gatctctggt cactgatttt cccacggacc tgccagcaac cgaagttttc taat        54

<210> SEQ ID NO 39
<211> LENGTH: 54
<212> TYPE: DNA
<213> ORGANISM: Artificial Sequence
<220> FEATURE:
<223> OTHER INFORMATION: Primer

<400> SEQUENCE: 39
ctagattagt ccgtgggaaa atcagtgacc agttcatcag attcatcaga atga        54

<210> SEQ ID NO 40
<211> LENGTH: 54
<212> TYPE: DNA
<213> ORGANISM: Artificial Sequence
<220> FEATURE:
<223> OTHER INFORMATION: Primer

<400> SEQUENCE: 40
gatctcattc tgatgaatct gatgaactgg tcactgattt cccacggac taat        54

<210> SEQ ID NO 41
<211> LENGTH: 10
<212> TYPE: PRT
<213> ORGANISM: Homo sapiens

<400> SEQUENCE: 41

Arg Gly Asp Ser Val Val Tyr Gly Leu Arg

```
<210> SEQ ID NO 42
<211> LENGTH: 10
<212> TYPE: PRT
<213> ORGANISM: Homo sapiens

<400> SEQUENCE: 42

Asp Gly Arg Gly Asp Ser Val Ala Tyr Gly
 1               5                  10

<210> SEQ ID NO 43
<211> LENGTH: 44
<212> TYPE: PRT
<213> ORGANISM: Homo sapiens

<400> SEQUENCE: 43

His Ser Asp Glu Ser Asp Glu Leu Val Thr Asp Phe Pro Thr Asp Leu
 1               5                  10                  15

Pro Ala Thr Glu Val Phe Thr Pro Val Val Pro Thr Val Asp Thr Tyr
            20                  25                  30

Asp Gly Arg Gly Asp Ser Val Val Tyr Gly Leu Arg
        35                  40

<210> SEQ ID NO 44
<211> LENGTH: 15
<212> TYPE: PRT
<213> ORGANISM: Homo sapiens

<400> SEQUENCE: 44

His Ser Asp Glu Ser Asp Glu Leu Val Thr Asp Phe Pro Thr Asp
 1               5                  10                  15

<210> SEQ ID NO 45
<211> LENGTH: 15
<212> TYPE: PRT
<213> ORGANISM: Homo sapiens

<400> SEQUENCE: 45

Leu Val Thr Asp Phe Pro Thr Asp Leu Pro Ala Thr Glu Val Phe
 1               5                  10                  15

<210> SEQ ID NO 46
<211> LENGTH: 15
<212> TYPE: PRT
<213> ORGANISM: Homo sapiens

<400> SEQUENCE: 46

Asp Leu Pro Ala Thr Glu Val Phe Thr Pro Val Val Pro Thr Val
 1               5                  10                  15

<210> SEQ ID NO 47
<211> LENGTH: 15
<212> TYPE: PRT
<213> ORGANISM: Homo sapiens

<400> SEQUENCE: 47

Phe Thr Pro Val Val Pro Thr Val Asp Thr Tyr Asp Gly Arg Ala
 1               5                  10                  15

<210> SEQ ID NO 48
<211> LENGTH: 16
<212> TYPE: PRT
<213> ORGANISM: Homo sapiens
```

```
<400> SEQUENCE: 48

Val Asp Thr Tyr Asp Gly Arg Ala Asp Ser Val Val Tyr Gly Leu Arg
 1               5                  10                  15

<210> SEQ ID NO 49
<211> LENGTH: 42
<212> TYPE: PRT
<213> ORGANISM: Bos taurus

<400> SEQUENCE: 49

His Ser Asp Glu Ser Asp Glu Val Asp Phe Pro Thr Asp Ile Pro Thr
 1               5                  10                  15

Ile Ala Val Phe Thr Pro Phe Ile Pro Thr Glu Ser Ala Asn Asp Gly
                20                  25                  30

Arg Gly Asp Ser Val Ala Tyr Gly Leu Lys
            35                  40

<210> SEQ ID NO 50
<211> LENGTH: 43
<212> TYPE: PRT
<213> ORGANISM: Sus scrofa

<400> SEQUENCE: 50

His Ser Asp Glu Ser Asp Glu Leu Val Thr Asp Phe Pro Thr Asp Thr
 1               5                  10                  15

Pro Ala Thr Asp Val Thr Pro Ala Val Pro Thr Gly Asp Pro Asn Asp
                20                  25                  30

Gly Arg Gly Asp Ser Val Val Tyr Gly Leu Arg
            35                  40

<210> SEQ ID NO 51
<211> LENGTH: 45
<212> TYPE: PRT
<213> ORGANISM: Oryctolagus cuniculus

<400> SEQUENCE: 51

His Gln Ser Asp Glu Ser Asp Glu Val Thr Val Tyr Pro Thr Glu Asp
 1               5                  10                  15

Ala Ala Thr Thr Val Phe Thr Gly Val Val Pro Thr Val Glu Thr Tyr
                20                  25                  30

Asp Gly Arg Gly Asp Ser Val Ala Tyr Arg Leu Lys Arg
            35                  40                  45

<210> SEQ ID NO 52
<211> LENGTH: 40
<212> TYPE: PRT
<213> ORGANISM: Rattus rattus

<400> SEQUENCE: 52

His Ser Asp Glu Ser Asp Glu Ser Phe Thr Ala Ser Thr Gln Ala Asp
 1               5                  10                  15

Val Leu Thr Pro Ile Ala Pro Thr Val Asp Val Pro Gly Arg Gly
                20                  25                  30

Asp Ser Leu Ala Tyr Gly Leu Arg
            35                  40

<210> SEQ ID NO 53
<211> LENGTH: 40
<212> TYPE: PRT
<213> ORGANISM: Mus musculus
```

<400> SEQUENCE: 53

His Ser Asp Glu Ser Asp Glu Thr Val Thr Ala Ser Thr Gln Ala Asp
 1               5                  10                  15

Thr Phe Thr Pro Ile Val Pro Thr Val Asp Val Pro Asn Gly Arg Gly
            20                  25                  30

Asp Ser Leu Ala Tyr Gly Leu Arg
        35                  40

<210> SEQ ID NO 54
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (11)
<223> OTHER INFORMATION: When Xaa at position 12 is an amino acid, Xaa
      at position 11 is absent
      or any amino acid
<220> FEATURE:
<221> NAME/KEY: VARIANT
<222> LOCATION: (12)
<223> OTHER INFORMATION: X is absent or any amino acid
<220> FEATURE:
<221> NAME/KEY: VARIANT
<222> LOCATION: (20)
<223> OTHER INFORMATION: Xaa is absent or any amino acid
<220> FEATURE:
<221> NAME/KEY: VARIANT
<222> LOCATION: (21)
<223> OTHER INFORMATION: When Xaa at position 20 is an amino acid, Xaa
      at position 21 is absent
      or any amino acid

<400> SEQUENCE: 54

His His Ser Asp Glu Ser Asp Glu Leu Val Xaa Xaa Phe Pro Thr Asp
 1               5                  10                  15

Leu Pro Ala Xaa Xaa Val Phe Thr Pro Val Val Pro Thr Val Asp
            20                  25                  30

<210> SEQ ID NO 55
<211> LENGTH: 20
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (10)
<223> OTHER INFORMATION: When Xaa at positions 11 and 12 are amino acids
      , Xaa at position 10 is
      absent or any amino acid
<220> FEATURE:
<221> NAME/KEY: VARIANT
<222> LOCATION: (11)
<223> OTHER INFORMATION: When Xaa at position 12 is an amino acid, Xaa
      at position 11 is absent
      or any amino acid
<220> FEATURE:
<221> NAME/KEY: VARIANT
<222> LOCATION: (12)
<223> OTHER INFORMATION: Xaa is absent or any amino acid

<400> SEQUENCE: 55

Pro Val Val Pro Thr Val Asp Thr Tyr Asp Xaa Xaa Xaa Ser Val Val
 1               5                  10                  15

Tyr Gly Leu Arg
        20

```
<210> SEQ ID NO 56
<211> LENGTH: 10
<212> TYPE: PRT
<213> ORGANISM: Artificial Sequence
<220> FEATURE:
<223> OTHER INFORMATION: Peptide

<400> SEQUENCE: 56

Arg Gly Asp Ser Val Val Tyr Gly Leu Arg
 1               5                  10
```